(12) United States Patent
Boveja et al.

(10) Patent No.: US 7,177,703 B2
(45) Date of Patent: *Feb. 13, 2007

(54) METHOD AND SYSTEM FOR PROVIDING PULSED ELECTRICAL STIMULATION TO SACRAL PLEXUS OF A PATIENT TO PROVIDE THERAPY FOR URINARY INCONTINENCE AND UROLOGICAL DISORDERS

(76) Inventors: Birinder R. Boveja, P.O. Box 210095, Milwaukee, WI (US) 53221; Angely Widhany, P.O. Box 210095, Milwaukee, WI (US) 53221

( * ) Notice: Subject to any disclaimer, the term of this patent is extended or adjusted under 35 U.S.C. 154(b) by 539 days.

This patent is subject to a terminal disclaimer.

(21) Appl. No.: 10/436,006

(22) Filed: May 11, 2003

(65) Prior Publication Data

US 2005/0143783 A1 Jun. 30, 2005

(51) Int. Cl.
*A61N 1/18* (2006.01)
(52) U.S. Cl. .......................... 607/118; 607/39; 607/40; 607/41
(58) Field of Classification Search ............ 607/39–41, 607/118, 133
See application file for complete search history.

(56) References Cited

U.S. PATENT DOCUMENTS

| | | | | |
|---|---|---|---|---|
| 3,870,051 A * | 3/1975 | Brindley | ...................... | 607/40 |
| 4,424,812 A * | 1/1984 | Lesnick | ....................... | 607/30 |
| 4,771,779 A * | 9/1988 | Tanagho et al. | ............... | 607/40 |
| 5,562,717 A | 10/1996 | Tippey et al. | .................. | 607/41 |
| 5,928,272 A | 7/1999 | Adkins et al. | ................ | 607/45 |
| 5,938,584 A | 8/1999 | Ardito et al. | ................ | 607/38 |
| 6,393,323 B1 | 5/2002 | Sawan et al. | ................. | 607/41 |
| 6,449,512 B1 | 9/2002 | Boveja | ........................ | 607/41 |
| 6,505,074 B2 | 1/2003 | Boveja et al. | ................ | 607/41 |
| 6,662,052 B1 | 12/2003 | Sarwal et al. | ................ | 607/59 |
| 6,735,474 B1 * | 5/2004 | Loeb et al. | ................... | 607/41 |
| 6,760,626 B1 | 7/2004 | Boveja | ........................ | 607/59 |
| 6,941,171 B2 * | 9/2005 | Mann et al. | .................. | 607/39 |
| 2001/0002441 A1 * | 5/2001 | Boveja | ........................ | 607/46 |
| 2002/0013613 A1 | 1/2002 | Haller et al. | ................. | 607/60 |
| 2002/0055761 A1 | 5/2002 | Mann et al. | .................. | 607/41 |
| 2002/0087192 A1 | 7/2002 | Barrett et al. | ................. | 607/2 |
| 2002/0183799 A1 | 12/2002 | Silvian | ........................ | 607/32 |
| 2003/0004553 A1 | 1/2003 | Grill et al. | ..................... | 607/40 |
| 2005/0049655 A1 * | 3/2005 | Boveja et al. | ................ | 607/58 |
| 2005/0143786 A1 * | 6/2005 | Boveja | ........................ | 607/45 |
| 2005/0187590 A1 * | 8/2005 | Boveja et al. | ................ | 607/45 |

* cited by examiner

*Primary Examiner*—Robert E. Pezzuto
*Assistant Examiner*—Tammie K. Heller

(57) ABSTRACT

A method and system for providing electrical pulses for neuromodulating sacral nerves of a patient utilizing an implantable stimulator. The implantable stimulator comprising a pulse generator module and a stimulus receiver module for coupling with an external stimulator. Control circuitry ensures selective operation of one pulse generator module. The external stimulator comprises a telemetry module for remotely activating (or de-activating) programs over the internet, to arrive at the optimal program for each patient. Once the optimal "dose" is titrated using the external stimulator, the implanted pulse generator can then be programmed to such parameters. The external stimulator in conjunction with the implanted stimulus receiver can override the implanted pulse generator, to provide extra dose of therapy or to conserve the implanted battery. The external stimulator is also networked to other computers. The external programmer may also comprise a global positioning system (GPS) module for determining patient location.

29 Claims, 36 Drawing Sheets

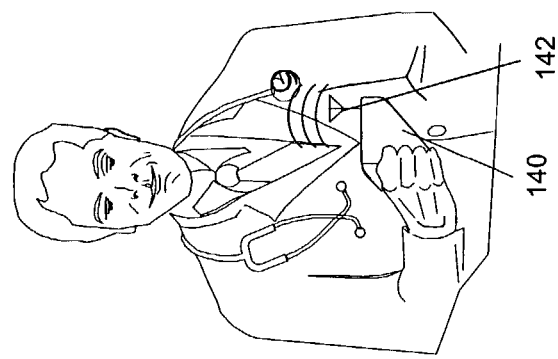
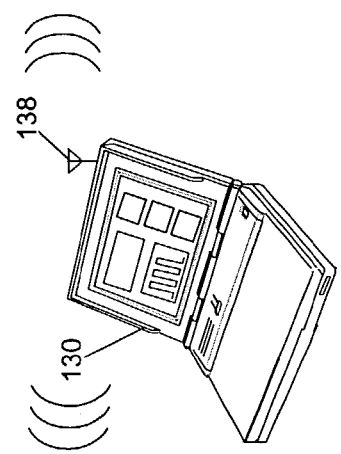
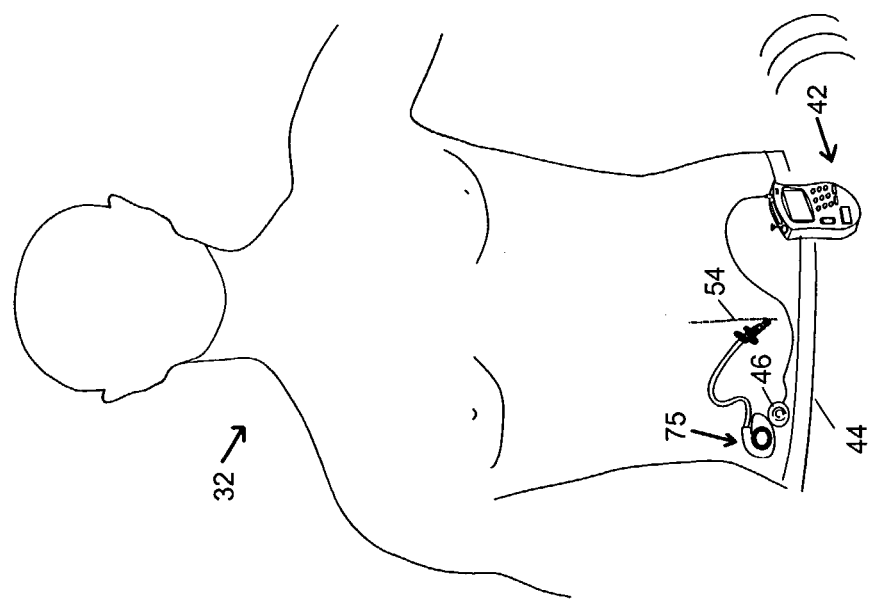
FIG. 6

| Axons from skin | Aα | Aβ | Aδ | C |
|---|---|---|---|---|
| Axons from muscles | Group I | II | III | IV |
| | | | | |
| Diameter (μm) | 13-20 | 6-12 | 1-5 | 0.2-1.5 |
| Speed (m/sec) | 80-120 | 35-75 | 5-30 | 0.5-2 |
| Sensory receptors | Proprioceptors of skeletal muscle | Mechanoreceptors of skin | Pain temperature | Temperature, pain, itch |

FIG. 11

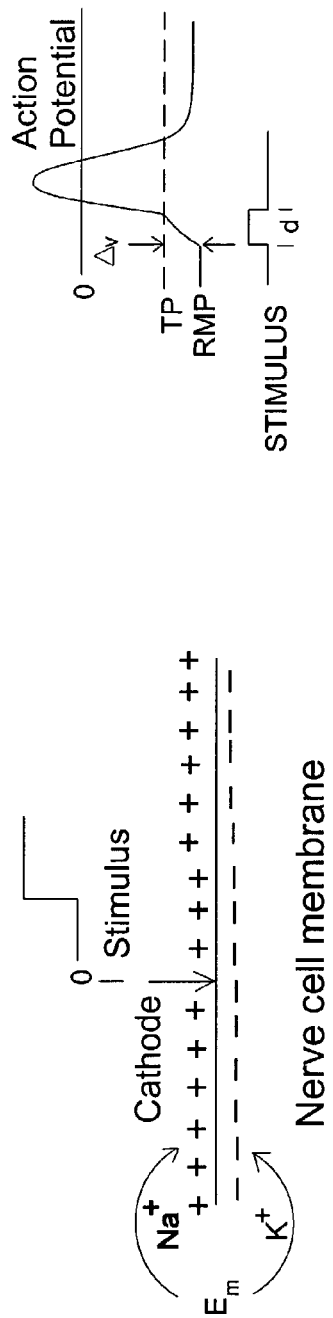
FIG. 12 B
FIG. 12 A
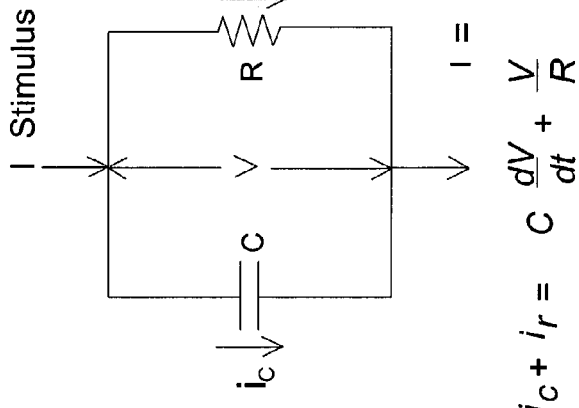
$$I = i_c + i_r = C\frac{dV}{dt} + \frac{V}{R}$$
FIG. 13

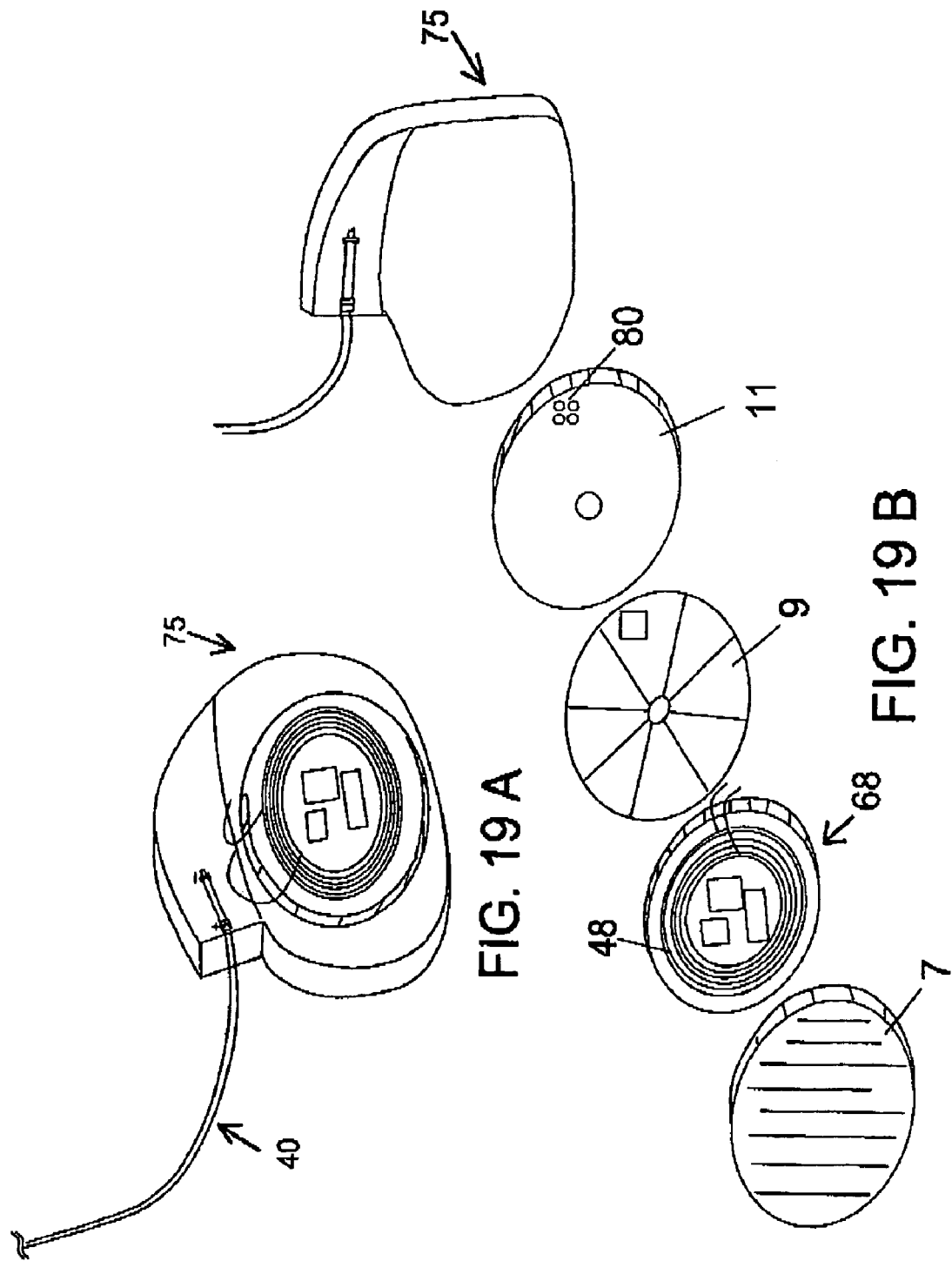

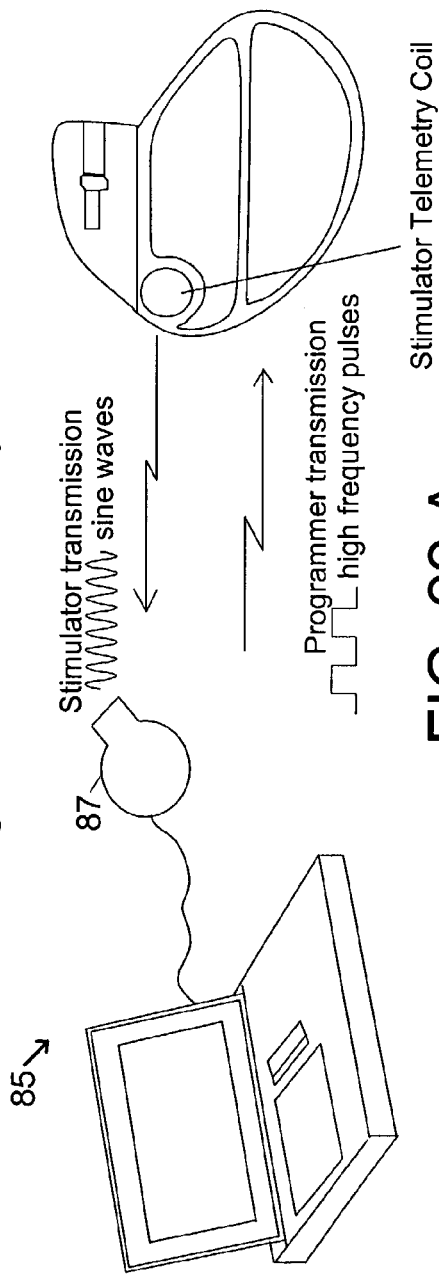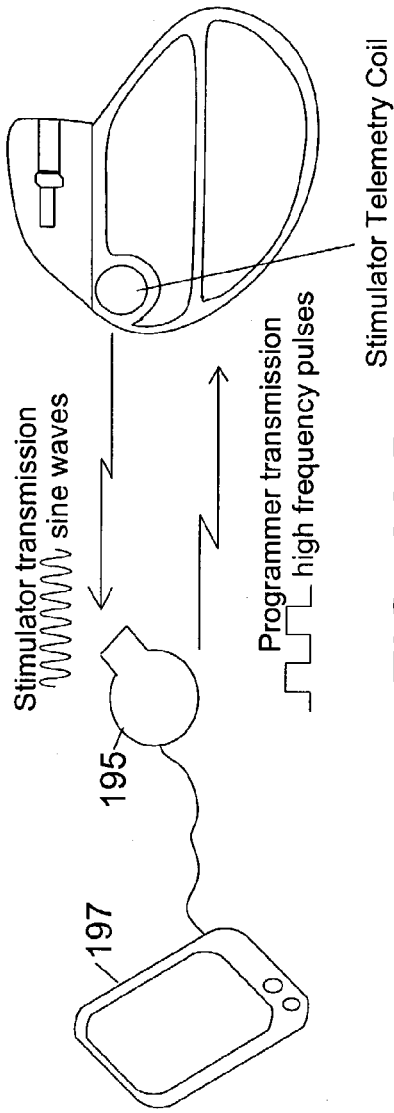
FIG. 22 A
FIG. 22 B

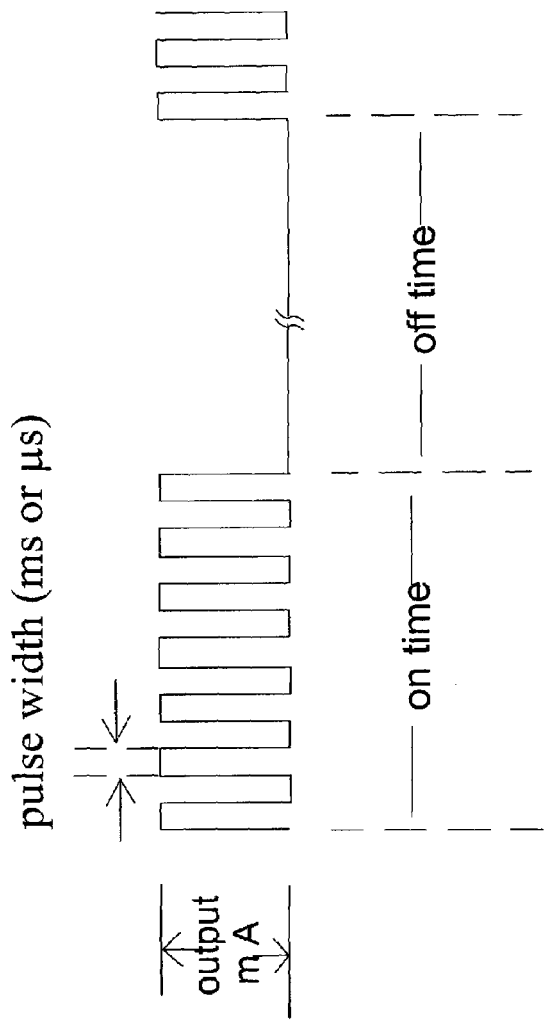
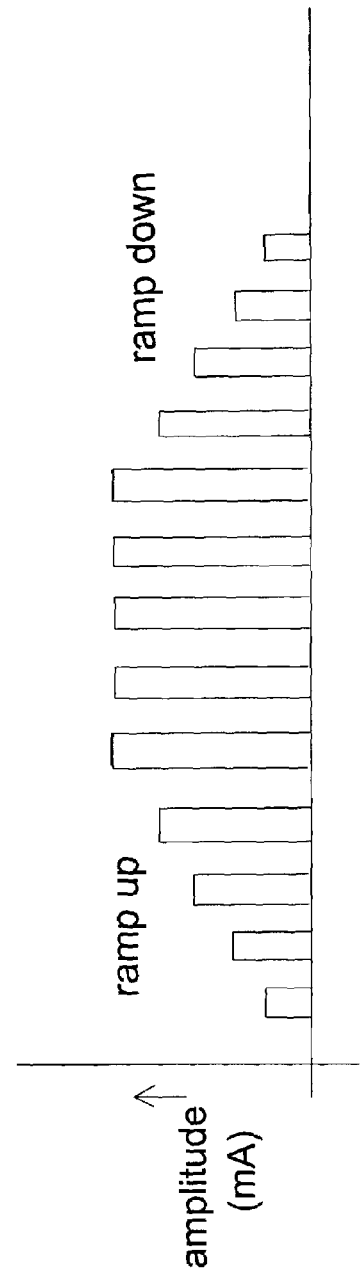
FIG. 27A
FIG. 27B

METHOD AND SYSTEM FOR PROVIDING PULSED ELECTRICAL STIMULATION TO SACRAL PLEXUS OF A PATIENT TO PROVIDE THERAPY FOR URINARY INCONTINENCE AND UROLOGICAL DISORDERS

FIELD OF INVENTION

The present invention relates to electrical neuromodulation therapy for medical disorders, more specifically pulsed electrical neuromodulation therapy for urinary incontinence and urological disorders utilizing an implanted stimulator comprising an implanted pulse generator and stimulus receiver.

BACKGROUND

Clinical research has shown utility of electrical nerve stimulation for urinary incontinence and a broad group of urological disorders. This invention is directed to method and system for providing pulsed electrical stimulation adjunct therapy for urological disorders. These urological disorders include, urinary incontinence, overflow incontinence, stress incontinence, neuro-urological disorder, bladder inflammation, bladder pain and the like.

With reference to prior art, U.S. Pat. No. 5,562,717 (Tippey et al) teaches an external system comprising a portable electrical stimulator which can be coupled to one or more electrodes for applying electrical stimulation signals to a patient. The signal generator being responsive to the instruction storage or programming device.

U.S. Pat. No. 6,393,323 B1 (Sawan et al) teaches a selective stimulation system which is composed of an internal stimulator implanted in the patient and operated with an external hand-held controller. The system being used to prevent bladder hyeperreflexia combined with a voiding signal generator generating a voiding signal for voiding the bladder.

U.S. Pat. No. 6,505,074 B2 (Boveja et al) is directed to an implanted stimulus receiver coupled with an external stimulator for providing neuromodulation therapy. U.S. Pat. No. 6,449,512 B1 (Boveja) is directed to an implantable pulse generator for providing electrical stimulation therapy for urological disorders. The implanted pulse generator, though convenient, has the disadvantage that the internal battery will not last for a desired period of time, which can lead to repeated surgeries for generator replacement. The inductively coupled implanted stimulus receiver overcomes the disadvantage of implanted battery replacement, but patient convenience is an issue since a primary coil has to be kept in close proximity to an implanted secondary coil. It would be desirable to have the advantages of both an IPG system and an inductively coupled system. The system and method disclosed, provides an improved method and system for adjunct therapy by providing a system that has the benefits of both systems, and has additional synergistic benefits not possible in the prior art. In the system of this invention, the patient can choose when to use an external inductively coupled system to conserve the battery life of the implanted module and receive higher levels of therapy.

The current application discloses an implanted medical device capable of being used as a programmable implanted pulse generator (IPG), or as a stimulus-receiver, for an inductively coupled system with power being supplied by an external stimulator, as is shown in FIGS. 1 and 2. The external stimulator also being remotely controllable from a distant location via the internet. Controlling circuitry within the device, makes the inductively coupled stimulator and the IPG operate in harmony with each other, as described later. For example, when stimulation is applied via the implanted stimulus receiver 68, the battery operated pulse generation module 70 is triggered to go into the "sleep" mode. Conversely, when programming pulses (also inductively coupled) are being applied to the battery operated pulse generator, the inductively coupled stimulation circuitry is disconnected.

In the method and system of the current invention, after the system is implanted in the patient, optimal stimulation parameters are "titrated" for the condition of the individual patent. Clinical research has shown that each patient is biologically unique and responds little bit differently to given stimulation. The inductively coupled stimulation part of the system is a very convenient method of adjusting the parameters for stimulation therapy, that would be optimally suited for each individual patient. Further, as shown in FIG. 3, the external stimulator has a telemetry module and can be controlled remotely via the internet. In one embodiment, numerous pre-determined programs are pre-packaged into the memory of the external stimulator 42. A physician situated remotely is able to selectively activate (and de-activate) selected pre-packaged (pre-determined) programs. As shown in FIGS. 4 and 5, the telemetry module within the external stimulator wirelessly communicates with a base station 2, either via a server (shown in FIG. 4) or directly (shown in FIG. 5). Also, as shown in FIG. 6, a physician in a remote location is able to interrogate and selectively program the external stimulator 42 via a server 130.

Once the appropriate stimulation parameters are determined by "trial and error", the battery operated portion of the implanted pulse generator can be programmed to the optimal electrical stimulation parameters via a programmer 85. For ideal therapy the electrical stimulation parameters need to be adjusted at regular intervals taking into account optimal benefits.

Another distinct advantage of the current system is that when the stimulation is performed via the external stimulator 42, the battery of the implanted pulse generator (IPG) 70 is conserved, extending the life of the implanted system.

Background of Neuromodulation

In considering the background of urinary urge incontinence, FIG. 7 shows a sagittal section of the human female pelvis showing the bladder 10 and urethra 13 in relation to other anatomic structures. Although FIG. 7 displays a female pelvis, the pulsed electrical stimulation therapy of the current invention applies equally to males. Urinary continence requires a relaxed bladder during the collecting phase and permanent closure of the urethra, whereas at micturition (urination), an intravesical pressure above the opening pressure of the simultaneously relaxing urethra has to be generated. These functions of the bladder 10 and urethra 13 are centrally coordinated and non-separable. At bladder filling, the sensation of urge is mediated by slowly adapting mechanoreceptors in the bladder wall and the same receptors provide the triggering signal for micturition and the main driving force for a sustained micturition contraction. The mechanoreceptors are, technically speaking, tension receptors. It has been found that they respond equally well to tension increases induced passively by bladder filling and those induced actively by a detrusor contraction. These receptors have high dynamic sensitivity and are easily activated by external pressure transients, as may occur during coughing or tapping of the abdominal wall. Their faithful response to active changes in bladder pressure is well illustrated.

When sufficiently activated, the mechanoreceptors trigger a coordinated micturition reflex via a center in the upper pons 388, as depicted schematically in FIG. 8. The reflex detrusor 392 (muscle in the wall of the urinary bladder) contraction generates an increased bladder pressure and an even stronger activation of the mechanoreceptors. Their activity in turn reinforces the pelvic motor output to the bladder 10, which leads to a further increase in pressure and more receptor activation and so on. In this way, the detrusor contraction is to a large extent self generating once initiated. Such a control mechanism usually is referred to as a positive feedback, and it may explain the typical all-or-nothing behavior of the parasympathetic motor output to the bladder 10. Once urine enters the urethra, the contraction is further enhanced by reflex excitation from urethral receptors. Quantitatively, the bladder receptors are most important.

A great advantage of the positive feedback system is that it ascertains a complete emptying of the bladder during micturition. As long as there is any fluid left in the lumen, the intravesical pressure will be maintained above the threshold for the mechanoreceptors and thus provide a continuous driving force for the detrusor. A drawback with this system is that it can easily become unstable. Any stimulus that elicits a small burst of impulses in mechanoreceptor afferents may trigger a full-blown micturition reflex. To prevent this from happening during the filling phase, the neuronal system controlling the bladder is equipped with several safety devices both at the spinal and supraspinal levels.

The best-known spinal mechanism is the reflex control of the striated urethral sphincter 90, which increases its activity in response to bladder mechanoreceptor activation during filling. An analogous mechanism is Edvardsen's reflex, which involves machanoreceptor activation of inhibitory sympathetic neurons to the bladder. The sympathetic efferents have a dual inhibitory effect, acting both at the postganglionic neurons in the vesical ganglia and directly on the detrusor muscle of the bladder 392. The sphincter and sympathetic reflexes are automatically turned off at the spinal cord level during a normal micturition. At the supraspinal level, there are inhibitory connections from the cerebral cortex and hypothalamus to the pontine micturition center. The pathways are involved in the voluntary control of continence. Other inhibitory systems seem to originate from the pontine and medullary parts of the brainstem with at least partly descending connections.

Bladder over-activity and urinary urge incontinence may result from an imbalance between the excitatory positive feedback system of the bladder 10 and inhibitory control systems causing a hyperexcitable voiding reflex. Such an imbalance may occur after macroscopic lesions at many sites in the nervous system or after minor functional disturbances of the excitatory or inhibitory circuits. Urge incontinence due to detrusor instability seldom disappears spontaneously. The symptomatic pattern also usually is consistent over long periods.

Based on clinical experience, subtypes of urinary incontinence include, Phasic detrusor instability and uninhibited overactive bladder. Phasic detrusor instability is characterized by normal or increased bladder sensation, phasic bladder contractions occurring spontaneously during bladder filling or on provocation, such as by rapid filling, coughing, or jumping. This condition results from a minor imbalance between the bladder's positive-feedback system and the spinal inhibitory mechanisms. Uninhibited overactive bladder is characterized by loss of voluntary control of micturition and impairment of bladder sensation. The first sensation of filling is experienced at a normal or lowered volume and is almost immediately followed by involuntary micturition. The patient does not experience a desire to void until she/he is already voiding with a sustained detrusor contraction and a concomitant relaxation of the urethra, i.e., a well-coordinated micturition reflex. At this stage, she/he is unable to interrupt micturition voluntarily. The sensory disturbance of these subjects is not in the periphery, at the level of bladder mechanoreceptors, as the micturition reflex occurs at normal or even small bladder volumes. More likely, the suprapontine sensory projection to the cortex is affected. Such a site is consistent with the coordinated micturition and the lack of voluntary control. The uninhibited overactive bladder is present in neurogenic dysfunction.

Since bladder over-activity results from defective central inhibition, it seems logical to improve the situation by reinforcing some other inhibitory system. Patients with stress and urge incontinence are difficult to treat adequately. Successful therapy of the urge component does not influence the stress incontinence. While an operation for stress incontinence sometimes results in deterioration of urgency component. Electro stimulation is a logical alternative in mixed stress and urge incontinence, since the method improves urethral closure as well as bladder control. Drug treatment often is insufficient and, even when effective, does not lead to restoration of a normal micturition pattern.

Neuromodulation is a technique that applies electrical stimulation to the sacral nerves, (a general diagram of spinal cord and sacral nerves 54 is shown in FIG. 9). The aim of this treatment modality is to achieve detrusor 392 inhibition by chronic electrical stimulation of afferent somatic sacral nerve fibers 54 via implanted electrodes coupled to an implanted stimulator.

The rationale of this treatment modality is based on the existence of spinal inhibitory systems that are capable of interrupting a detrusor 392 contraction. Inhibition can be achieved by electrical stimulation of afferent anorectal branches of the pelvic nerve, afferent sensory fibers in the pudendal nerve and muscle afferents from the limbs. Most of these branches and fibers reach the spinal cord via the dorsal roots of the sacral nerves 54. Of the sacral nerve roots the $S_3$ root is the most practical for use in chronic electrical stimulation, although $S_4$ and $S_2$ along with $S_3$ may be stimulated.

As shown in conjunction with FIGS. 10 and 11, most nerves in the human body are composed of thousands of fibers, of different sizes designated by groups A, B and C. A peripheral nerve, for example, may have approximately 100,000 fibers of the three different types, each carrying signals. Each axon or fiber of that nerve conducts only in one direction, in normal circumstances. The A and B fibers are myelinated (i.e., have a myelin sheath, constituting a substance largely composed of fat, whereas the C fibers are unmyelinated.

A commonly used nomenclature for peripheral nerve fibers, using Roman and Greek letters, is given in the table below:

| Group | External Diameter (μm) | Conduction Velocity (m/sec) |
| --- | --- | --- |
| Myelinated Fibers | | |
| Aα or IA | 13–20 | 80–120 |
| Aβ: IB | 10–15 | 60–75 |
| II | 5–15 | 30–75 |
| Aγ | 3–8 | 15–40 |
| Aδ or III | 3–8 | 10–30 |
| B | 1–3 | 5–15 |
| Unmyelinted fibers | | |
| C or IV | 0.2–1.5 | 0.5–2.5 |

The diameters of group A and group B fibers include the thickness of the myelin sheaths. Group A is further subdivided into alpha, beta, gamma, and delta fibers in decreasing order of size. There is some overlapping of the diameters of the A, B, and C groups because physiological properties, especially the form of the action potential, are taken into consideration when defining the groups. The smallest fibers (group C) are unmyelinated and have the slowest conduction rate, whereas the myelinated fibers of group B and group A exhibit rates of conduction that progressively increase with diameter. Group B fibers are not present in the nerves of the limbs; they occur in white rami and some cranial nerves.

Compared to unmyelinated fibers, myelinated fibers are typically larger, conduct faster, have very low stimulation thresholds, and exhibit a particular strength-duration curve or respond to a specific pulse width versus amplitude for stimulation. The A and B fibers can be stimulated with relatively narrow pulse widths, from 50 to 200 microseconds (μs), for example. The A fiber conducts slightly faster than the B fiber and has a slightly lower threshold. The C fibers are very small, conduct electrical signals very slowly, and have high stimulation thresholds typically requiring a wider pulse width (300–1,000 μs) and a higher amplitude for activation. Selective stimulation of only A and B fibers is readily accomplished. The requirement of a larger and wider pulse to stimulate the C fibers, however, makes selective stimulation of only C fibers, to the exclusion of the A and B fibers, virtually unachievable inasmuch as the large signal will tend to activate the A and B fibers to some extent as well.

Stimulation of individual fibers is shown in conjunction with FIGS. 12A, 12B and 13. A nerve cell can be excited by increasing the electrical charge within the neuron, thus increasing the membrane potential inside the nerve with respect to the surrounding extracellular fluid. The threshold stimulus intensity is defined as that value at which the net inward current (which is largely determined by Sodium ions) is just greater than the net outward current (which is largely carried by Potassium ions), and is typically around −55 mV inside the nerve cell relative to the outside (critical firing threshold). If however, the threshold is not reached, the graded depolarization will not generate an action potential and the signal will not be propagated along the axon. This fundamental feature of the nervous system i.e., its ability to generate and conduct electrical impulses, can take the form of action potentials, which are defined as a single electrical impulse passing down an axon. This action potential (nerve impulse or spike) is an "all or nothing" phenomenon, that is to say once the threshold stimulus intensity is reached, an action potential will be generated.

FIG. 12A illustrates a segment of the surface of the membrane of an excitable cell. Metabolic activity maintains ionic gradients across the membrane, resulting in a high concentration of potassium ($K^+$) ions inside the cell and a high concentration of sodium ($Na^+$) ions in the extracellular environment. The net result of the ionic gradient is a transmembrane potential that is largely dependent on the $K^+$ gradient. Typically in nerve cells, the resting membrane potential (RMP) is slightly less than 90 mV, with the outside being positive with respect to inside.

To stimulate an excitable cell, it is only necessary to reduce the transmembrane potential by a critical amount. When the membrane potential is reduced by an amount ΔV, reaching the critical or threshold potential (TP); Which is shown in FIG. 12B. When the threshold potential (TP) is reached, a regenerative process takes place: sodium ions enter the cell, potassium ions exit the cell, and the transmembrane potential falls to zero (depolarizes), reverses slightly, and then recovers or repolarizes to the resting membrane potential (RMP).

For a stimulus to be effective in producing an excitation, it must have an abrupt onset, be intense enough, and last long enough. These facts can be drawn together by considering the delivery of a suddenly rising cathodal constant-current stimulus of duration d to the cell membrane as shown in FIG. 12B. Cell membranes can be reasonably well represented by a capacitance C, shunted by a resistance R as shown by a simplified electrical model in diagram 13.

When the stimulation pulse is strong enough, an action potential will be generated and propagated. Immediately after the spike of the action potential there is a refractory period when the neuron is either unexcitable (absolute refractory period) or only activated to sub-maximal responses by supra-threshold stimuli (relative refractory period). The absolute refractory period occurs at the time of maximal Sodium channel inactivation while the relative refractory period occurs at a later time when most of the $Na^+$ channels have returned to their resting state by the voltage activated $K^+$ current. The refractory period has two important implications for action potential generation and conduction. First, action potentials can be conducted only in one direction, away from the site of its generation, and secondly, they can be generated only up to certain limiting frequencies.

These electrical signals travel along the nerve fibers. The information in the nervous system is coded by frequency of firing rather than the size of the action potential. In neuromodulation, the entire innervation system should be intact. As shown schematically in FIG. 14, the procedure consists of placing the distal portion of the lead 40 with electrodes 61,62 in one of the sacral foraman as close to the pelvic plexus and pudendal nerve as possible and connecting the lead 40 to the implanted stimulator 75, which is placed subcutaneously. The hypothesis behind neuromodulation of the sacral roots (sensory and motor) is to correct, by the use of regulating electrical impulses, the dys-synergic activities of the cholinergic, adrenergic, and motor reflex pathways that initiate vesical storage and micturition. Although some theories have been developed that explain the effects of neuromodulation, most of the results are based on empiric findings in human studies. Some animal experiments and electrophysiologic studies in humans show there is a spinal inhibitory action through the afferent branches of the pelvic and pudendal nerves. It is not clear whether neuromodulation primarily influences the micturition center located near the thalamus in the brain. Some maintain that there is a direct correction of the dys-synergis of the pelvic floor (pudendal nerve) by influencing the abnormal contractility of the pelvic floor.

A neurophysiological explanation for the effectiveness of this treatment modality in detrusor instability is based on animal experiments and electrophysiological studies in humans. Electrical stimulation for the treatment of urinary incontinence has evolved over the past 40 years. The mechanism of action of electrical stimulation was investigated initially in animal models. Over 100 years ago, Griffiths demonstrated relaxation of a contracted detrusor during stimulation of the proximal pudendal nerve in the cat model and further work clarified the role of pudendal afferents in relation of the detrusor. Spinal inhibitory systems capable of interrupting a detrusor contraction can be activated by electrical stimulation of afferent anorectal branhes of the pelvic nerve, afferent sensory fibers in the pudendal nerve and muscle afferents from the limbs. The effectiveness of neuromodulation in humans has been objectively demonstrated by urodynamic improvement, especially in light of the fact that such effects have not been noted in drug trials.

Neuromodulation also acts on neural reflexes but does so internally by stimulation of the sacral nerves 54. Sacral nerves 54 stimulation is based on research dedicated to the understanding of the voiding reflex as well as the role and influence of the sacral nerves 54 on voiding behavior. This research led to the development of a technique to modulate dysfunctional voiding behavior through sacral nerve stimulation. It is thought that sacral nerve stimulation induces reflex mediated inhibitory effects on the detrusor through afferent and/or efferent stimulation of the sacral nerves 54.

Even though the precise mechanism of action of electrical stimulation in humans is not fully understood, it has been shown that sensory input traveling through the pudendal nerve can inhibit detrusor activity in humans. It is generally believed that non-implanted electrical stimulation works by stimulating the pudendal nerve afferents, with the efferent outflow causing contraction of the striated pelvic musculature. There is also inhibition of inappropriate detrusor activity, though the afferent mechanism has yet to be clarified. There is consensus that the striated musculature action is able to provide detrusor inhibiton in this setting, though data supporting this hypotheses are lacking.

In summary, the rationale for neuromodulation in the management of such patients is the observation that stimulation of the sacral nerves via electrical stimulation can inhibit inappropriate neural reflex behavior.

The system and methods disclosed herein also may be appropriate for the treatment of other conditions, as disclosed in a co-pending application filed on May 11, 2003 entitled, METHOD AND SYSTEM FOR PROVIDING PULSED ELECTRICAL STIMULATION TO A CRANIAL NERVE OF A PATIENT TO PROVIDE THERAPY FOR NEUROLOGICAL AND NEUROPSYCHIATRIC DISORDERS, the disclosure of which is incorporated herein by reference.

SUMMARY OF THE INVENTION

The current invention discloses a method and system for neuromodulating sacral nerves with an implantable stimulator, to provide therapy for urinary incontinence and urological disorders. The implantable stimulator of the current invention comprising a pulse generator module and a stimulus receiver module for coupling with an external stimulator.

One object of the present invention is to provide an improved system and method for pulsed electrical stimulation to provide therapy for urinary incontinence and urological disorders. Another object is to derive at the optimal pulsed electrical stimulation dose for the individual patient in a convenient way, where an attending physician can activate (or de-activate) the therapy program remotely. A further object is to extend the service life of the implanted stimulator, whereby more intensive therapy can be given if appropriate, and surgical interventions for replacement of implanted stimulators are reduced.

Accordingly in one aspect of the invention, the system comprises an implantable stimulator and a lead, an external stimulator, and a programmer. The implantable stimulator comprising a pulse generator module deriving power from an implanted battery, and a stimulus receiver module deriving power from an external stimulator. Control circuitry ensures selective operation of one pulse generator module. The implanted pulse generator module delivering electric stimulation therapy to a sacral nerves according to predetermined parameters programmed by the programmer. The implanted stimulator system operates according to a program stored in the memory. Upon receiving stimulus energy from an inductively coupled external stimulator, the implanted pulse generator goes into "sleep" mode. The length of time that the internal battery operated pulse generator stays in "sleep" mode is a programmable parameter.

In another aspect of the invention, the external stimulator is adapted to be remotely controllable via the internet. The external stimulator comprises a number of predetermined programs. Several of these programs are locked out to the patient, and can be activated (or de-activated) remotely via the internet, by the medical staff. Since each patient is unique, different stimulation parameters can be tried by the patient, without the patient having to travel to the clinic for programming. Once the optimal stimulation therapy program is identified, the patient can have the implanted stimulator programmed to the optimal settings.

In another aspect of the invention, the external stimulator may be used in conjunction with the implanted stimulus receiver in order to extend the service life of the implantable stimulator or to temporarily deliver more aggressive therapy for specific situations.

In another aspect of the invention, with some modification in the circuitry, the implantable stimulator may be used as a re-chargable implantable pulse generator to provide therapy for urinary incontinence and urological disorders.

In yet another aspect of the invention the implantable stimulator may be programmerless, whereby limited programmability can be realized with a magnet.

In another aspect of the invention, the external stimulator comprises a telemetry module and is adapted to be networked.

In yet another aspect of the invention, the programmer or the external stimulator comprises a global positioning system (GPS) module for patient location.

BRIEF DESCRIPTION OF THE DRAWINGS

For the purpose of illustrating the invention, there are shown in accompanying drawing forms which are presently preferred, it being understood that the invention is not intended to be limited to the precise arrangement and instrumentalities shown.

FIG. 6 is a diagram showing a physician communicating with a remote external stimulator from a hand-held device through a server.

FIG. 11 is a table showing details of nerve fiber characteristics.

FIGS. 12A and 12B show an action potential across a nerve fiber.

FIG. 13 is a schematic illustration of electrical properties of the nerve fiber membrane.

FIGS. 19A and 19B show assembly features of the implantable portion of the system.

FIGS. 22A and 22B are diagrams showing communication of programmer with the implanted stimulator.

FIG. 27A is a diagram depicting a pulse train.

FIG. 27B is a diagram depicting ramping up and down of the pulse train.

DETAILED DESCRIPTION OF THE INVENTION

The following description is of the current embodiment for carrying out the invention. This description is not to be taken in a limiting sense, but is made merely for the purpose of describing the general principles of the invention.

Figure 1:
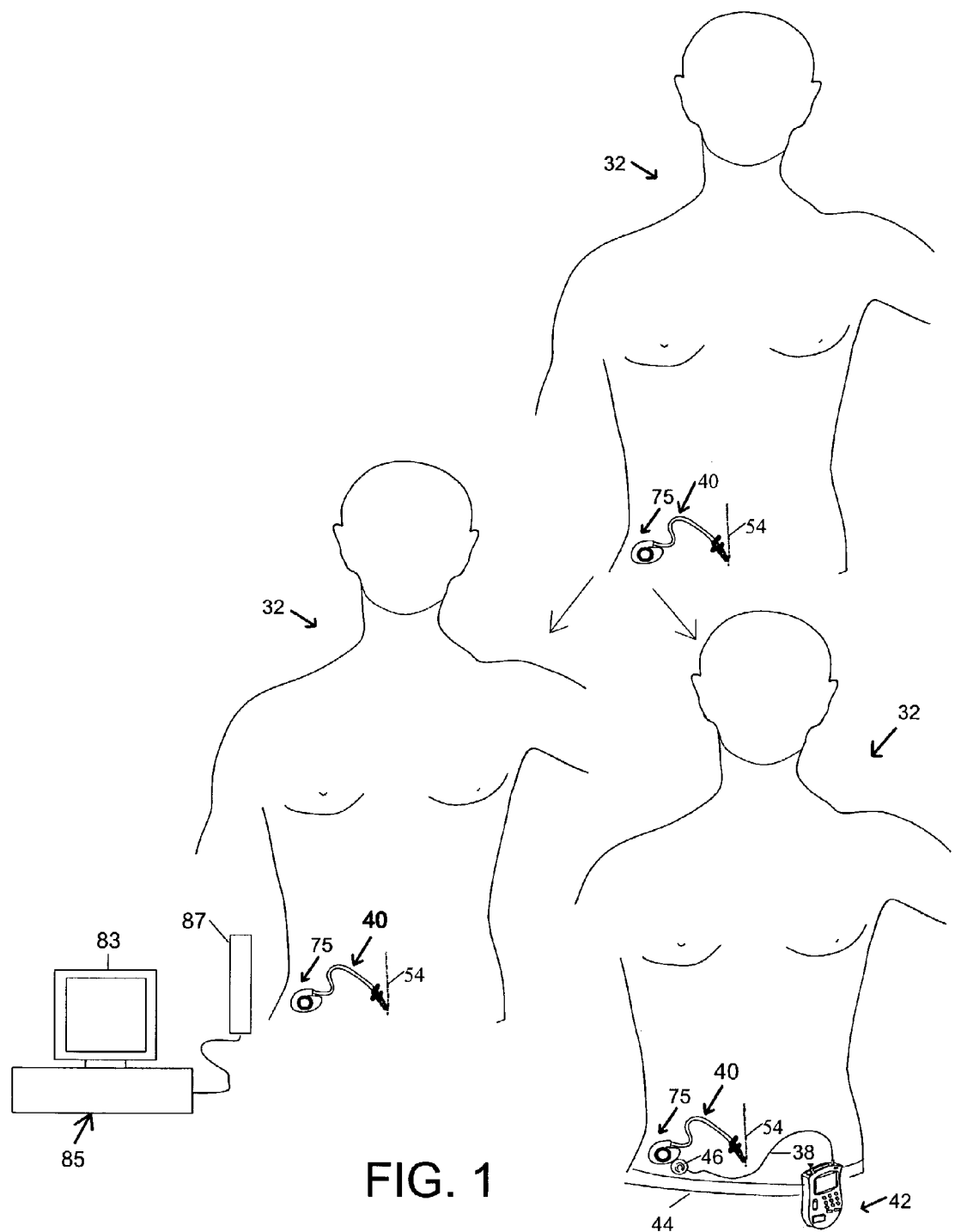
FIG. 1 diagrammatically illustrates the concept of an implanted pulse generator (IPG) being used with an external stimulator or a programmer.

As shown in FIG. 1, the system of the present invention comprises, an implanted stimulator 75, an implanted lead 40, an external stimulator 42, and an external programmer 85.

Figure 2:
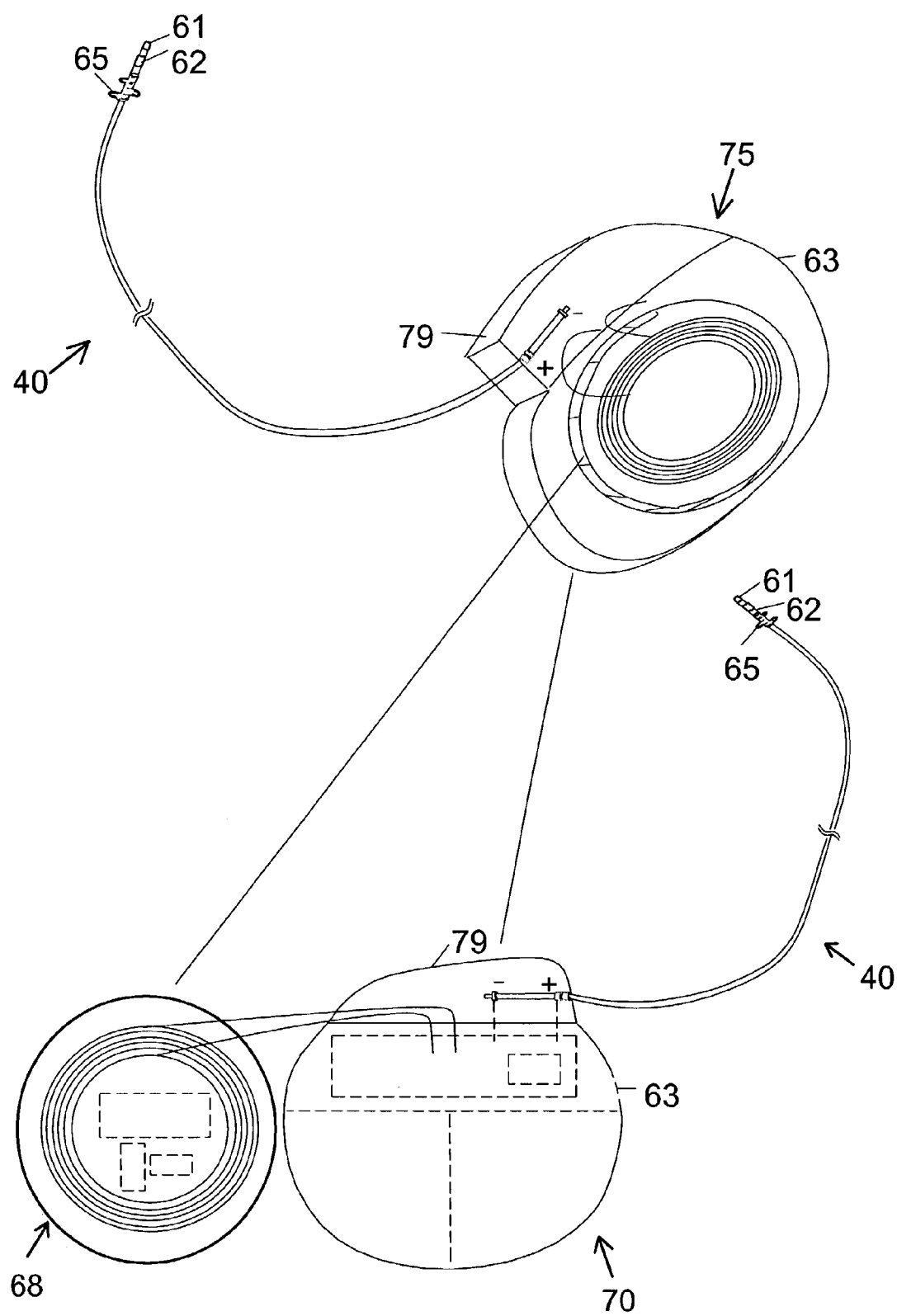
FIG. 2 is a diagram showing the implantable components of the system.
Figure 3:
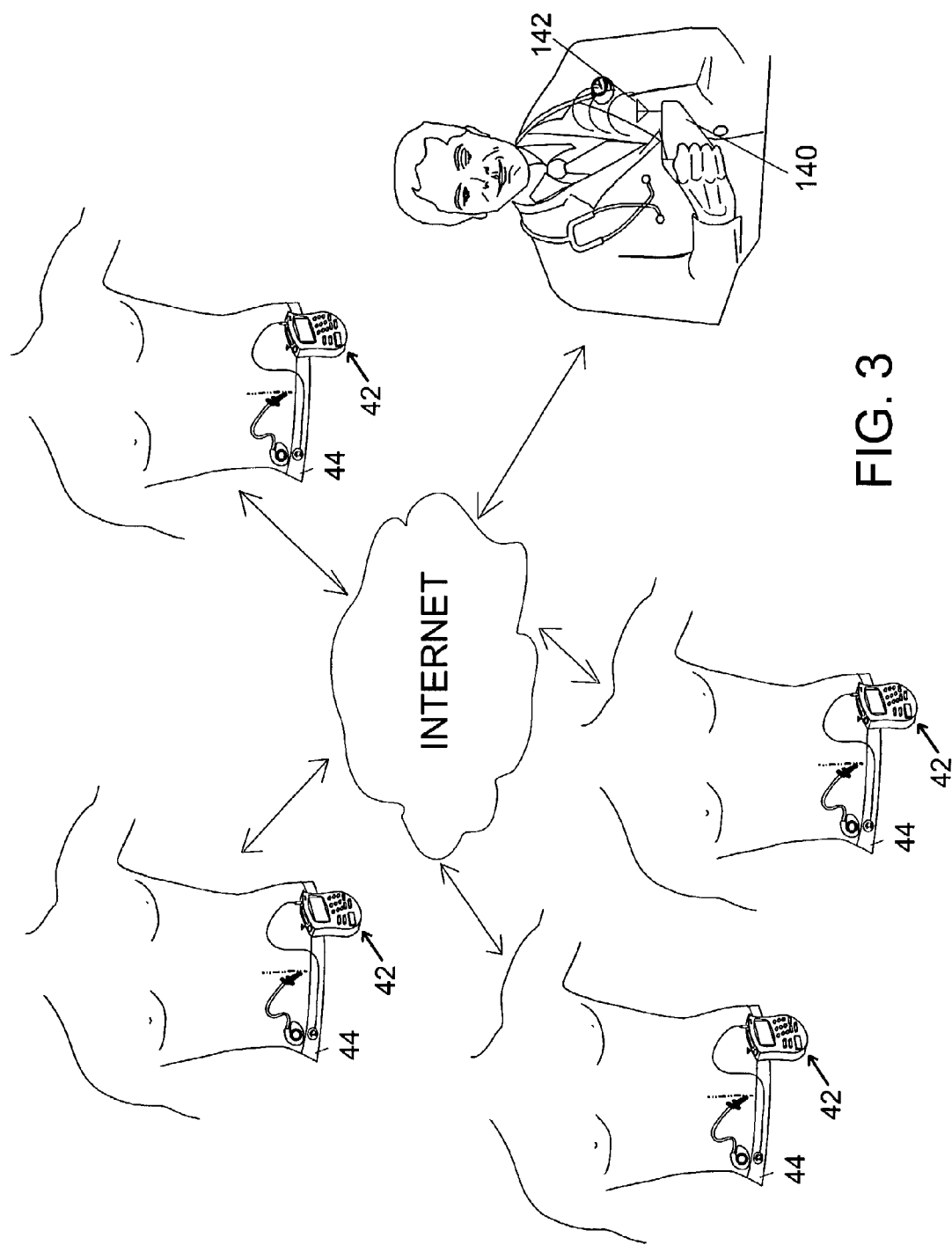
FIG. 3 diagrammatically shows physician's control of external stimulator device over internet.
Figure 4:
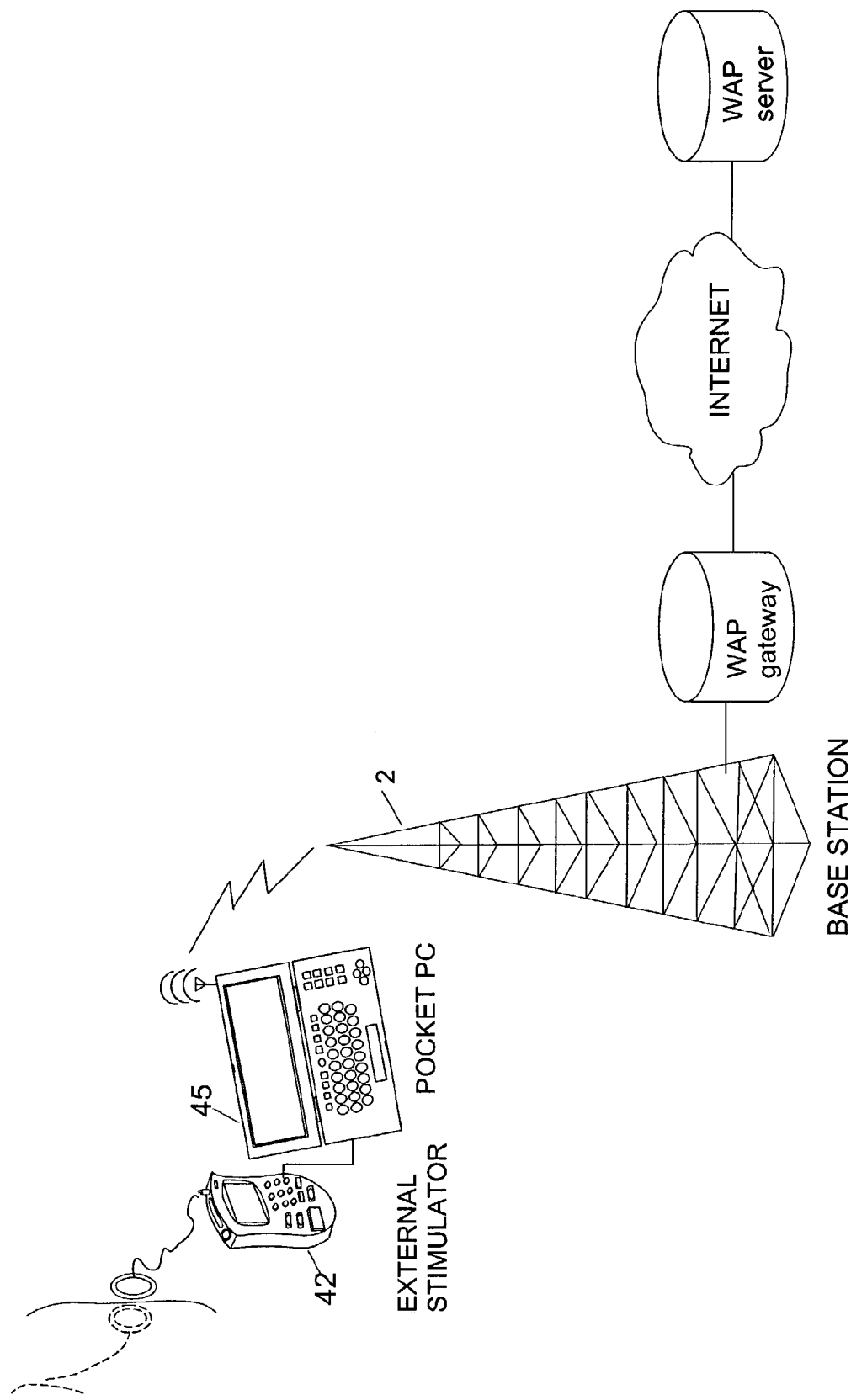
FIG. 4 is a diagram showing communication of the external stimulator with the base station through a PC.
Figure 5:
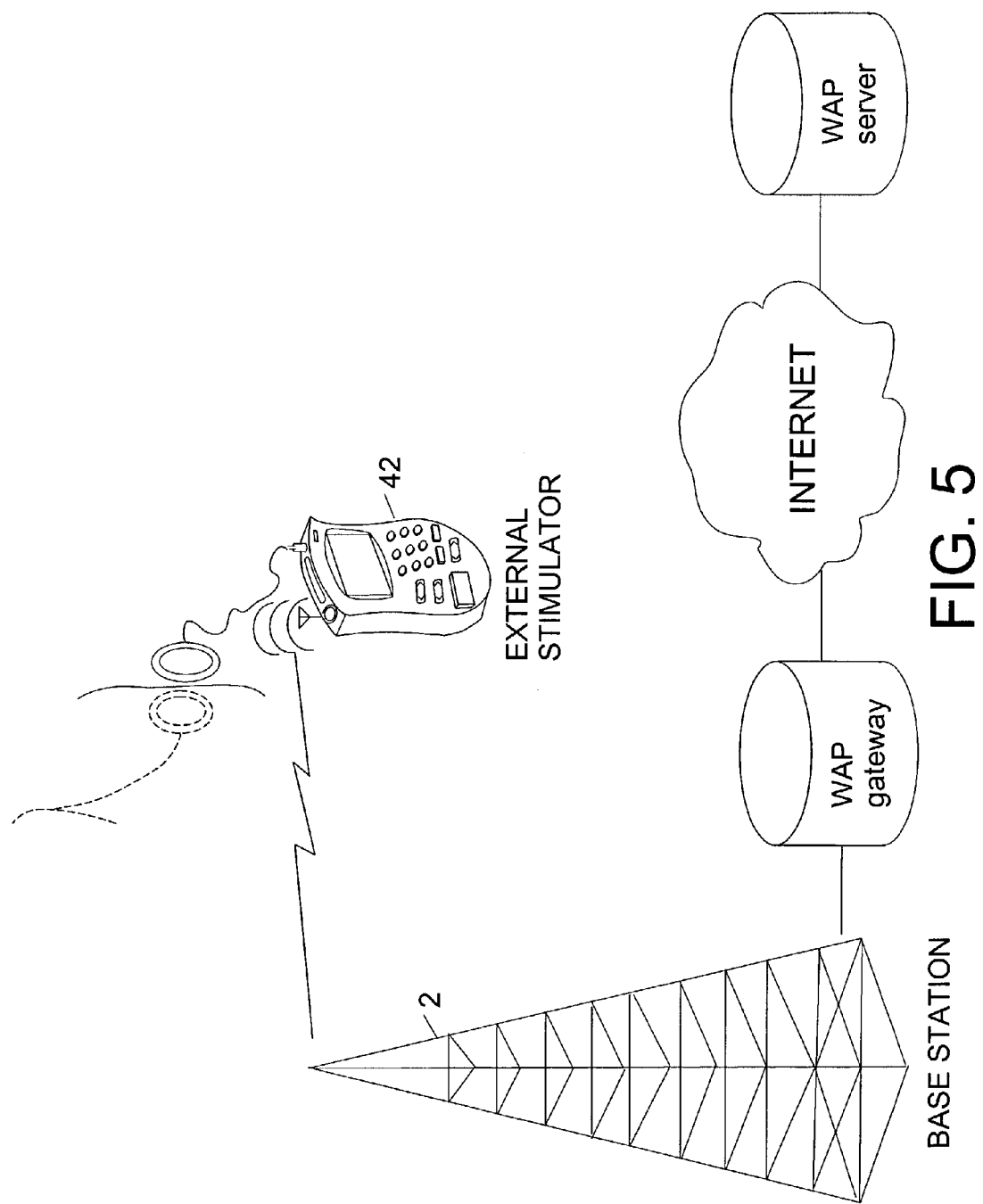
FIG. 5 is a diagram showing communication of the external stimulator directly with a base station.
Figure 7:
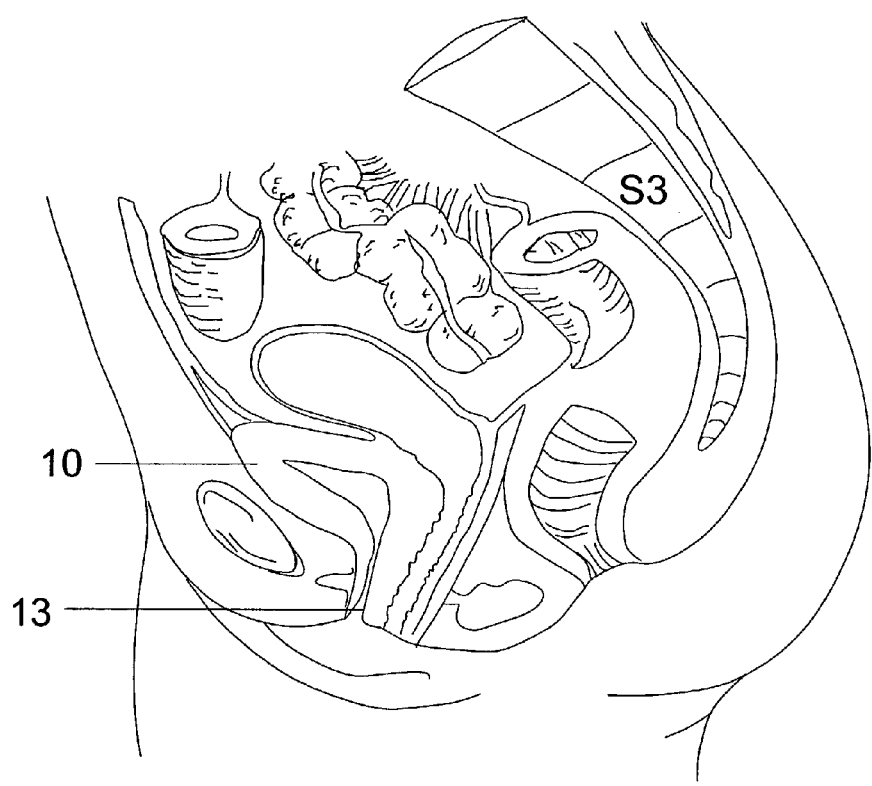
FIG. 7 is a diagram of the sagittal section of the female pelvis, showing the relationship between various anatomic structures.
Figure 8:
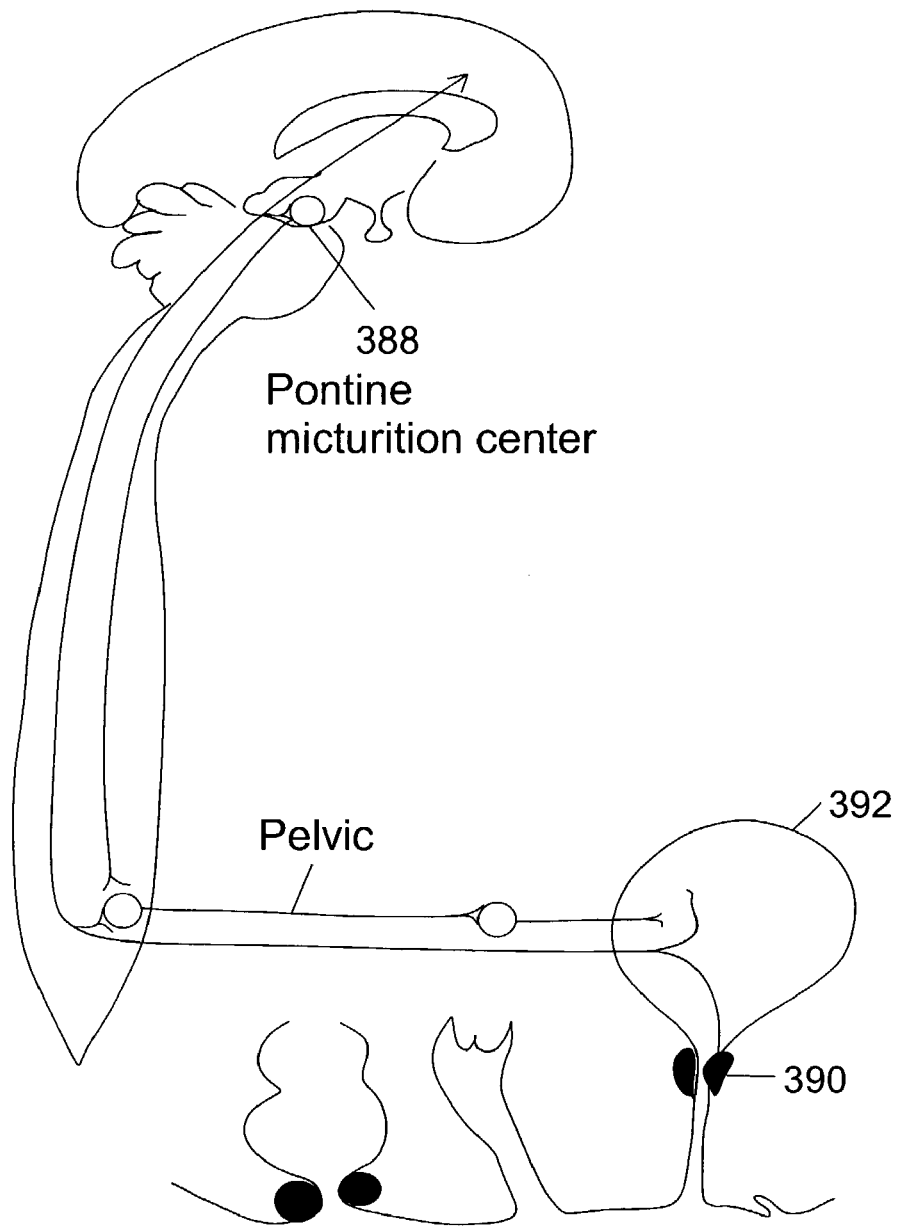
FIG. 8 is a schematic diagram showing physiological control of micturition.
Figure 9:
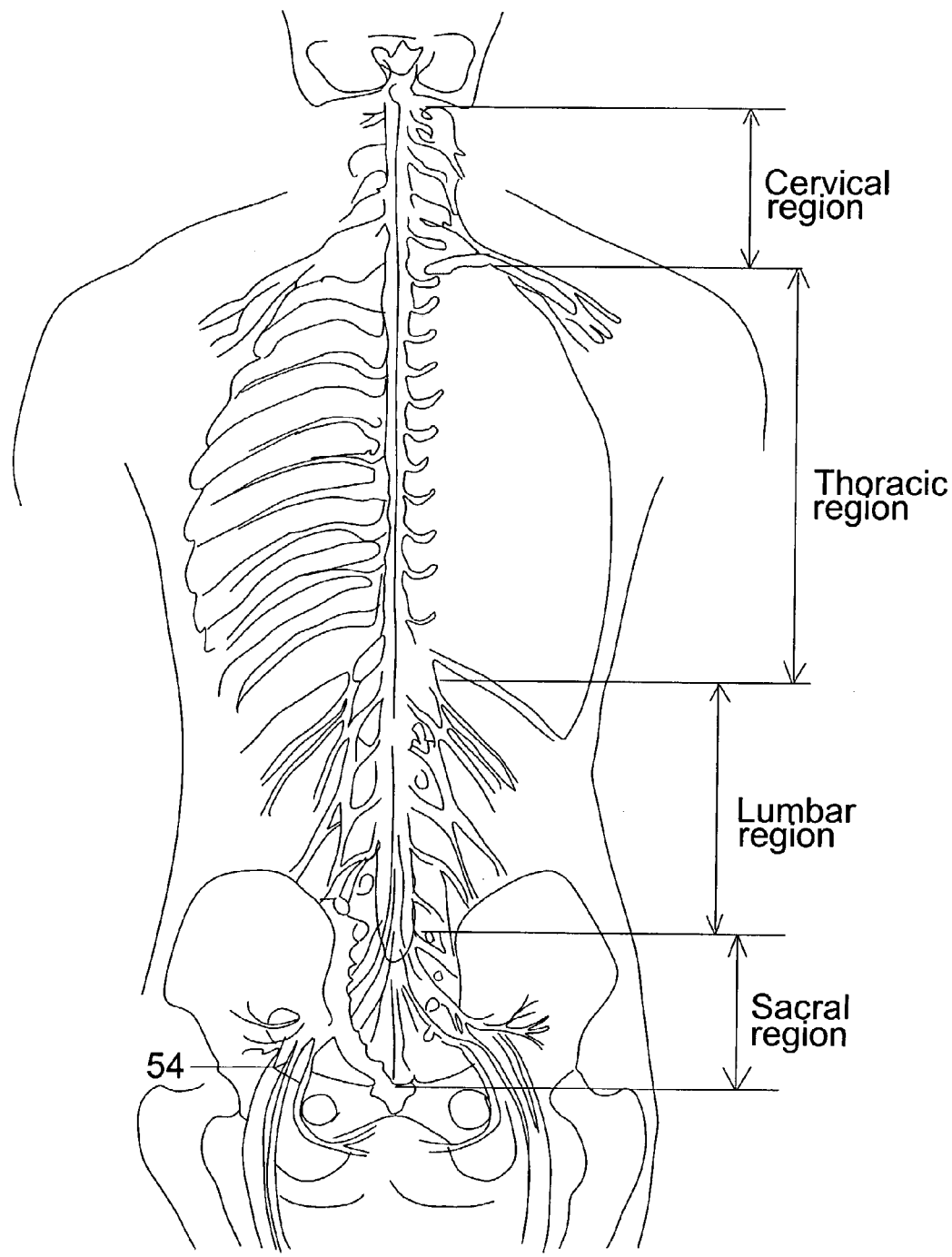
FIG. 9 is a diagram showing anatomic relationships of spinal nerves and sacral region.
Figure 10:
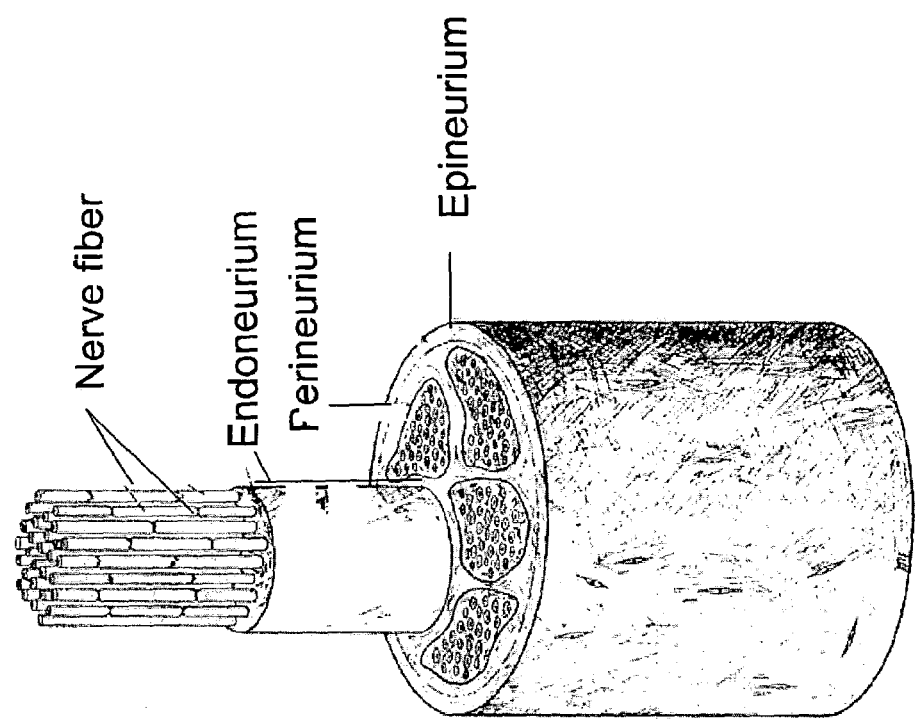
FIG. 10 is a diagram of the structure of a nerve.

As is shown in FIG. 2, the implantable stimulator 75 contains two stimulator assemblies 68,70 which operate in a coordinated fashion because of the control circuitry coordinating the two assemblies. The stimulus receiver module 68, which is outside of the titanium can 63 is similar to an inductively coupled stimulation system. The second assembly, which is encased in a titanium can 63 is the pulse generator (IPG) 70 deriving power from an implanted battery. Control circuitry ensures that the two assemblies operate correctly.

Figure 15:
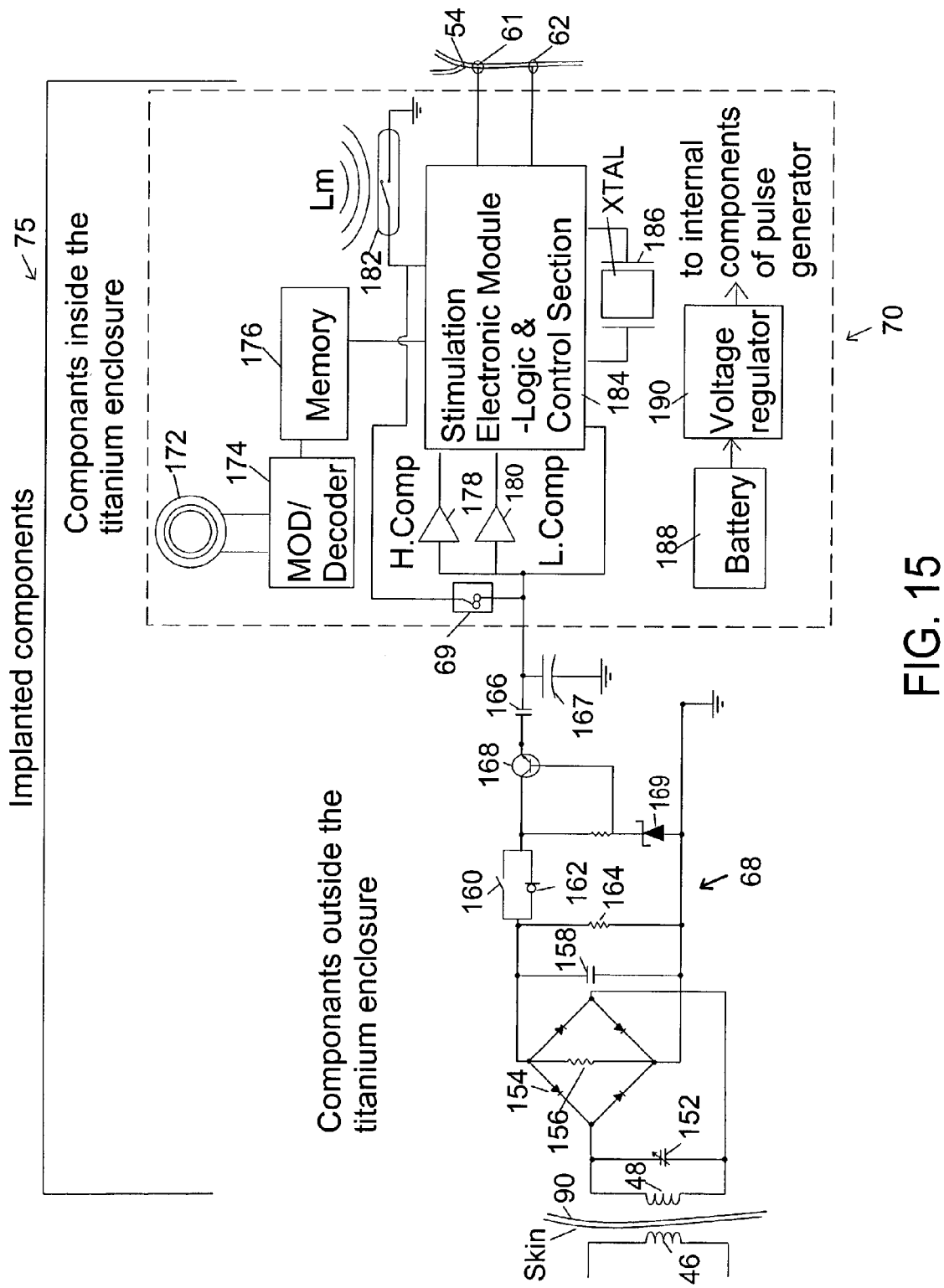
FIG. 15 is a schematic and functional block diagram showing the components and their relationships to the implantable pulse generator.

A simplified schematic and block diagram of the implantable stimulator 75 is shown in FIG. 15. The inductively coupled stimulus receiver module 68 is shown in left part of the diagram in FIG. 15. The battery operated portion 70 is shown on right side of the diagram. Much of the circuitry included within this embodiment of the implanted pulse generator 70 is realized on single application specific integrated circuit (ASIC). This allows the overall size of the IPG 70, to be quite small and readily housed within a suitable hermetically-sealed case, such as one made of titanium 63. Using CMOS technology and monolithic design, the analog and digital functions are integrated on a silicon chip approximately 5 mm×5 mm in size. Hybrid technology being used as a reliable connection technology for the wiring of the IC with non-integrated discrete components (like quartz oscillators, tantalium capacitors, coils of transmission, reed contacts, etc).

Figure 14:
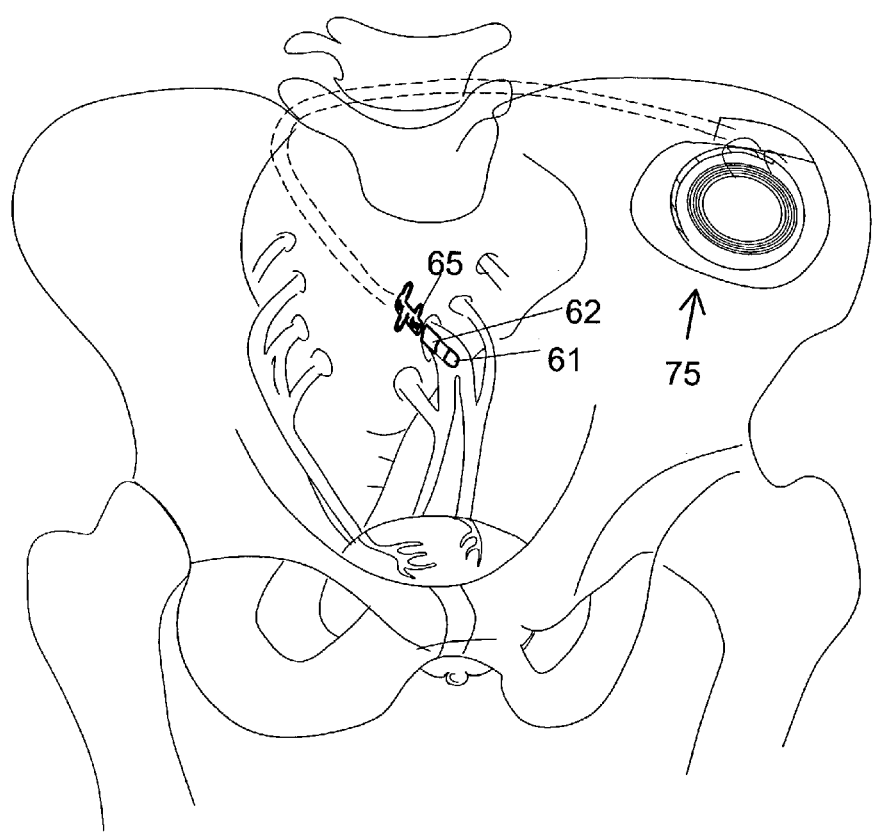
FIG. 14 is a diagram showing schematically the placement of the implanted lead in contact with the sacral nerves.

The implantable stimulator 75 is implanted in a patient in the usual fashion, by making an incision for positioning the lead 40. A second incision is also made for placement of the implantable stimulator 75. Using surgical dissection, the lead 40 is advanced and positioned such that the electrodes 61, 62 are in contact with the sacral nerves 54 to be electrically stimulated (shown in conjunction with FIG. 14). The distal portion of the lead 40 is anchored, and the terminal end of the lead 40 is tunneled subcutaneously and connected to the implantable stimulator 75. The implantable stimulator 75 is secured to the tissues, and both incisions are surgically closed in the usual manner. Stimulation can begin once the tissues are healed from surgery.

Once implanted, in the system and method of this invention, stimulation can be performed either via an external stimulator 42 in conjunction with the stimulus receiver module 68, or via the implanted pulse generator 70 according to parameters which are programmed via an external programmer 85.

In one aspect of the invention, the physician can asses the stimulation parameters in terms of efficacy and tolerability to the patient, by using the external stimulator 42 in conjunction with the stimulus receiver module 68. Advantageously, the external stimulator 42 is networked, and can be controlled by a physician via the internet, from a distant location. Once the optimal stimulation parameters are assessed and the stimulation dose is "titrated" via an optimal program, the stimulation parameters can by programmed into the implanted pulse generator 70 using the external programmer 85.

The sacral nerves 54 stimulation for a particular patient, can be performed in one of two ways with the external stimulator 42. One method is to activate one of several "pre-determined" programs. A second method is to "custom" program the electrical parameters which can be selectively programmed, for the individual patient. The electrical parameters that can be individually programmed, include variables such as pulse amplitude, pulse width, pulses per second, modulation type, modulation index, stimulation on-time, and stimulation off-time.

The system of the present invention is designed such that when stimulation is applied via the external stimulator 42 through the primary (external) coil 46, and is picked up by the implanted (secondary) coil 48, the battery operated stimulation module (IPG) 70 is temporarily suspended. This is accomplished through the comparator circuitry 178, 180 which sends a control signal to the controller 184, causing the battery operated stimulator module to suspend operation and go into "sleep mode". The length of time for this "sleep mode" is programmable with the external programmer 85.

The external stimulator 42 comprises numerous (say 200) pre-packaged programs. In addition, "customized" programs can be generated and stored in one of the several memories available in the external stimulator 42. New programs can be loaded into the external stimulator 42, preferably as described in U.S. Pat. No. 6,366,814 B1, incorporated herein by reference. Each pre-packaged program comprises a unique combination of electrical pulse stimulation parameters such as pulse amplitude, pulse width, number of pulses per second, on-time and off-time.

The following are examples of least aggressive therapy.
Program: 1.5 volt output, 0.2 msec pulse width, 10 Hz frequency, 30 sec ON time, 30 sec OFF time, in repeating cycles.
Program: 2.0 volt output, 0.2 msec pulse width, 15 Hz frequency, 1 minute ON time, 30 sec OFF time, in repeating cycles.

The following are examples of more aggressive level of therapy.
Program: 2.5 volt output, 0.25 msec pulse width, 20 Hz frequency, continuously ON.
Program: 2.5 volt output, 0.3 msec pulse width, 30 Hz frequency, 30 sec ON time, 30 sec OFF time, in repeating cycles.

The following are examples of patient "locked-out" programs.
Program: 3.5 volt output, 0.25 msec pulse width, 25 Hz frequency, 5 minutes ON time, 1 minute OFF time, in repeating cycles.
Program: 4.5 volt output, 0.3 msec pulse width, 30 Hz frequency, 2 minutes ON time, 2 minutes OFF time, in repeating cycles.

The above are examples of the predetermined programs for urinary incontinence applications. The actual parameter settings for any given patient may deviate from the above.

In addition to the use of predetermined programs, a second method is to "custom" program the electrical parameters which can be selectively programmed, for specific disease state of the individual patient. The electrical parameters which can be individually programmed, include variables such as pulse amplitude, pulse width, frequency of stimulation, modulation type, modulation index, stimulation on-time, and stimulation off-time. Table three below defines the approximate range of parameters,

TABLE 3

Electrical parameter range delivered to the nerve

| PARAMER | RANGE |
| --- | --- |
| Pulse Amplitude | 0.1 Volt–10 Volts |
| Pulse width | 20 µS–5 mSec. |
| Frequency | 5 Hz–200 Hz |
| On-time | 10 Secs–24 hours |
| Off-time | 10 Secs–24 hours |

It being understood that the signals generated by the external pulse generator and transmitted via the primary coil 46 (antenna) are larger, because the attenuation factor between the primary coil 46 and secondary coil 48 is approximately 10–20 times, depending upon the distance, and orientation between the two coils. Accordingly, the range of transmitted signals of the external pulse generator are approximately 10–20 times larger than shown in Table 3.

In the method and system of current invention, much of the stimulation parameters "dose" titration, and patient tolerability to "aggressive" stimulation can be performed without the patient having to go to the clinic or physician's office for programming. Many of the pre-packaged programs are initially locked out to the patient. During the course of therapy, the physician can selectively activate the few programs that the patient is going to try for evaluating efficacy of therapy and patient tolerance. The remote activation and de-activation of selected pre-packaged programs may be performed by the medical staff from a distant location using cable modem and internet, as described in a co-pending application Ser. No. 09/794,530. Alternatively, the medical staff can activate (and de-activate) selected pre-packaged programs over the wireless internet as disclosed in another co-pending application Ser. No. 09/837,565. Both of the disclosures being incorporated herein in their entirety by reference. Such activation and de-activation of selected pre-packaged programs may be used in "titrating" the optimal dose for therapy.

Patient tolerance to nerve stimulation therapy can vary widely. Once the particular patient's tolerance and response is "characterized", the stimulation parameters can be programmed into the battery operated module of the implanted stimulator 75 via an external programmer 85.

With reference to FIG. 15, for the functioning of the inductively coupled stimulus receiver 68, a primary (external) coil 46 is placed in close proximity to secondary (implanted) coil 48. Referring to the left portion of FIG. 15, the amplitude and pulse width modulated radiofrequency signals from the primary coil 46 are electromagnetically coupled to the secondary (implanted) coil 48 in the implanted unit 75. The two coils, 46 and 48 thus act like an air-gap transformer. The system having means for proximity sensing between the coils and feedback regulation of signals as described more fully in U.S. Pat. No. 6,473,652 B1, which is incorporated herein in its entirety by reference.

The combination of capacitor 152 and inductor 48 tunes the receiver circuitry to the high frequency of the transmitter with capacitor 152. The receiver is made sensitive to frequencies near the resonant frequency of the tuned circuit and less sensitive to frequencies away from the resonant frequency. A diode bridge 154 rectifies the alternating voltages. Capacitor 158 and resistor 164 filter out the high-frequency component of the receiver signal, and leaves the current pulse of the same duration as the bursts of the high-frequency signal. A zenor diode 169 is used for regulation and capacitor 166 blocks any net direct current.

Figure 18A:
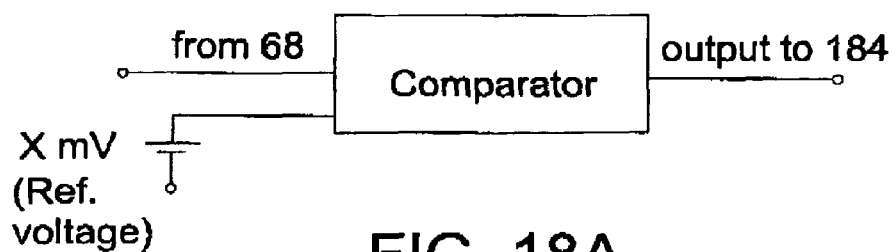
FIGS. 18A, 18B and 18C show output pulses from a comparater when input exceeds a reference voltage.
Figure 18B:
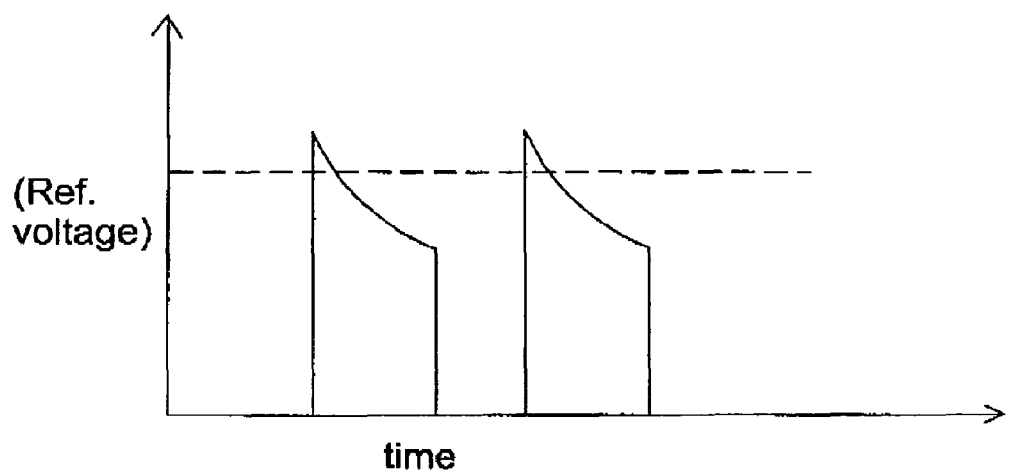
Figure 18C:
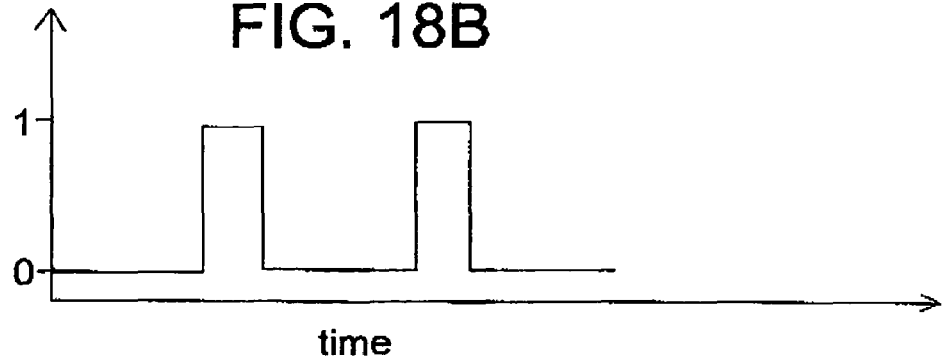

As shown in conjunction with FIG. 18A, the pulses generated from the stimulus receive circuitry 68 are compared to a reference voltage, which is programmed in the stimulator. When the voltage of incoming pulses exceeds the reference voltage (FIG. 18B), the output of the comparator 178,180 sends a digital pulse 89 (shown in FIG. 18C) to the stimulation electric module 184. At this predetermined level, the high threshold comparator 178 fires and the controller 184 suspends any stimulation from the implanted pulse generator 70. The implanted pulse generator 70 goes into a "sleep" mode for a predetermined period of time. In the presently preferred embodiment, the level of voltage needed for the battery operated stimulator to go into "sleep" mode is a programmable parameter. The length of time, the pulse generator 70 remains in "sleep" mode is also a programmable parameter. Therefore, advantageously the external stimulator in conjunction with the inductively coupled part of the stimulator 68 can be used as much as needed by the patient, and prescribed by the physician.

In the preferred embodiment, the external stimulator 42 is networked using the internet, giving the attending physician full control for activating and de-activating selected programs. Using "trial and error" various programs for electrical pulse therapy can be "titrated" for the individual patent. Also, by using the external stimulator 42, the battery 188 of the implanted stimulator unit 75 can be greatly extended. Further, even after the battery is depleted, the system can still be used for neuromodulation using the stimulus receiver module 68, and the external stimulator 42.

At some point, the battery operated portion of the implanted pulse generator 70 is programmed with the external programmer 85, using a modified PC and a programming wand 87, as is shown in FIGS. 22A and 22B.

Figure 16:
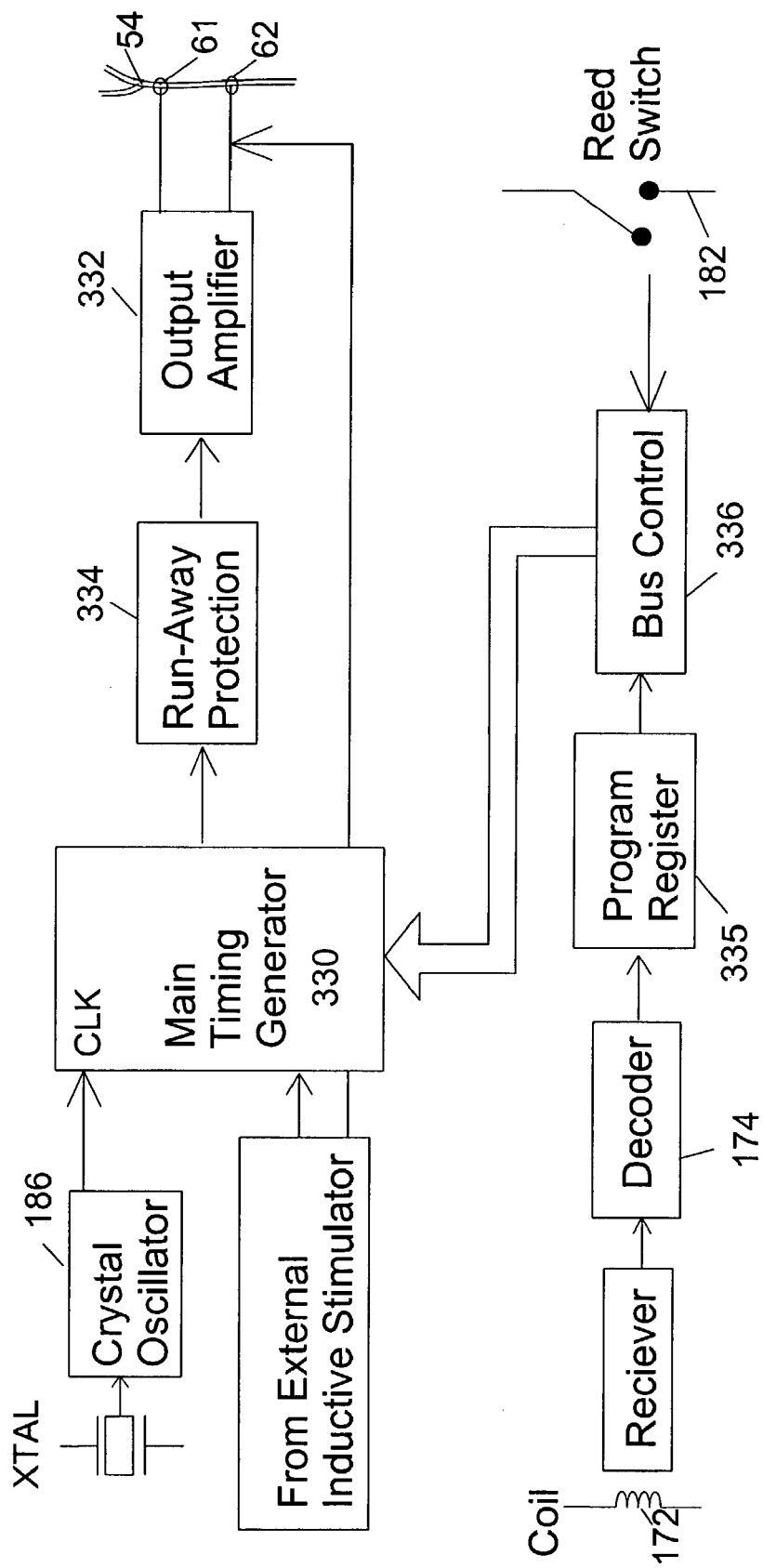
FIG. 16 is a block diagram showing details of implanted pulse generator.
Figure 17:
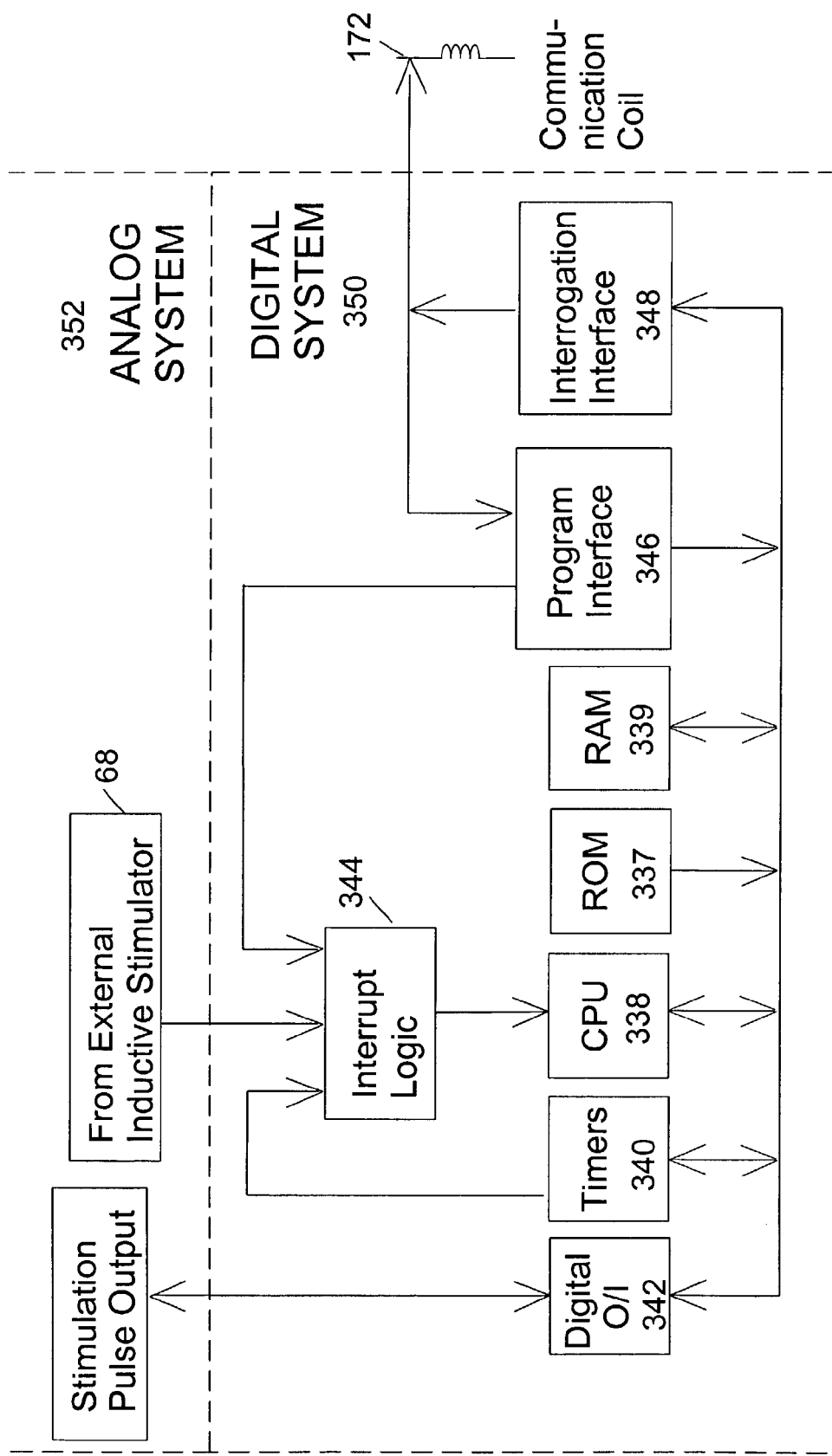
FIG. 17 is a block diagram showing details of implantable circuitry.

The battery operated portion of the system is shown on the right side of FIG. 15 and is described in conjunction with FIGS. 16 and 17. The stimulation electronic module 184 comprises both digital and analog circuits. The main timing generator 330 (shown in FIG. 16), controls the timing of the analog output circuitry for delivering neuromodulating pulses to the sacral nerves 54, via output amplifier 332. Main timing generator 330 receiving clock pulses from crystal oscillator 186. The main timing generator 330 also receiving input from inductively coupled circuitry 68 and programmer 85 via coil 172. FIG. 17 highlights other portions of the digital system such as CPU 338, ROM 337, RAM 339, Program interface 346, Interrogation interface 348, Timers 340, and Digital O/I 342.

FIG. 19A shows a picture of one embodiment of the implantable stimulator 75. FIG. 19B shows the pulse generator with some of the components used in assembly in an exploded view. These components include a coil cover 7, the secondary coil 48 and associated components, a magnetic shield 9, and a coil assembly carrier 11. The coil assembly carrier 11 has at least one positioning detail 80 located between the coil assembly and the feed through for positioning the electrical connection. The positioning detail 80 secures the electrical connection.

Figure 20A:
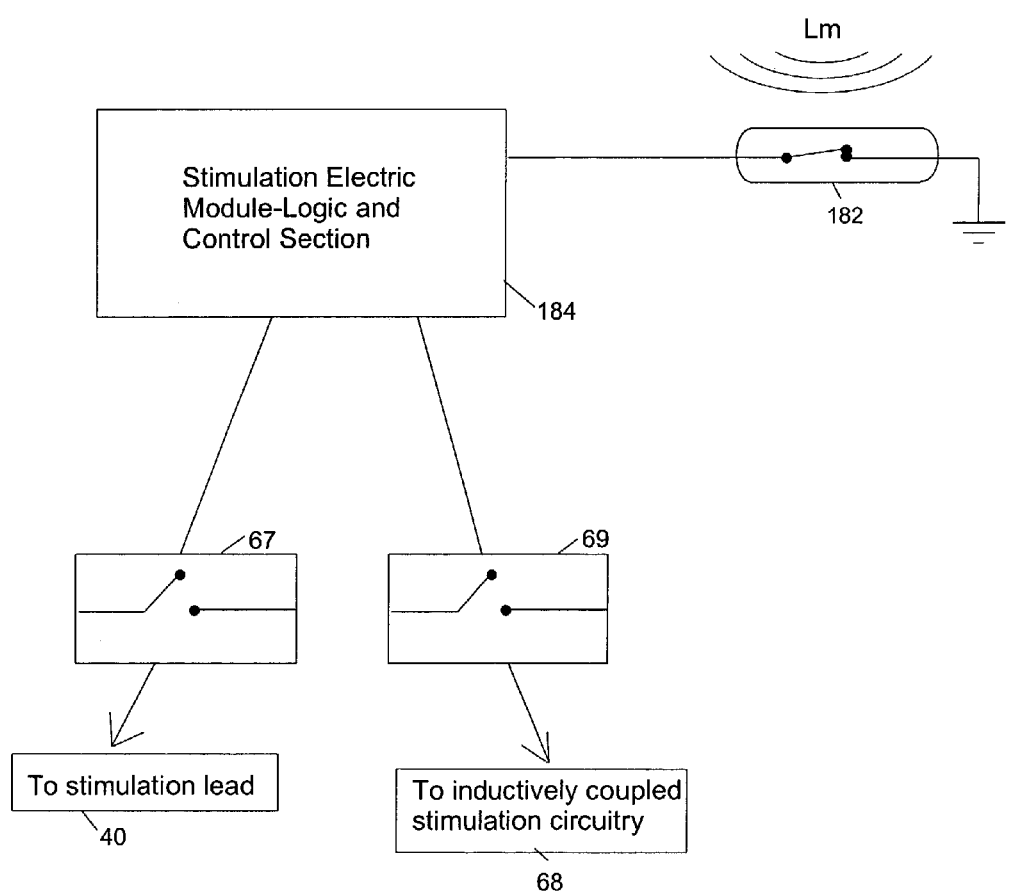
FIGS. 20A and 20B are simplified block diagrams showing the switching relationships between the inductively coupled and battery powered assemblies of the pulse generator.
Figure 20B:
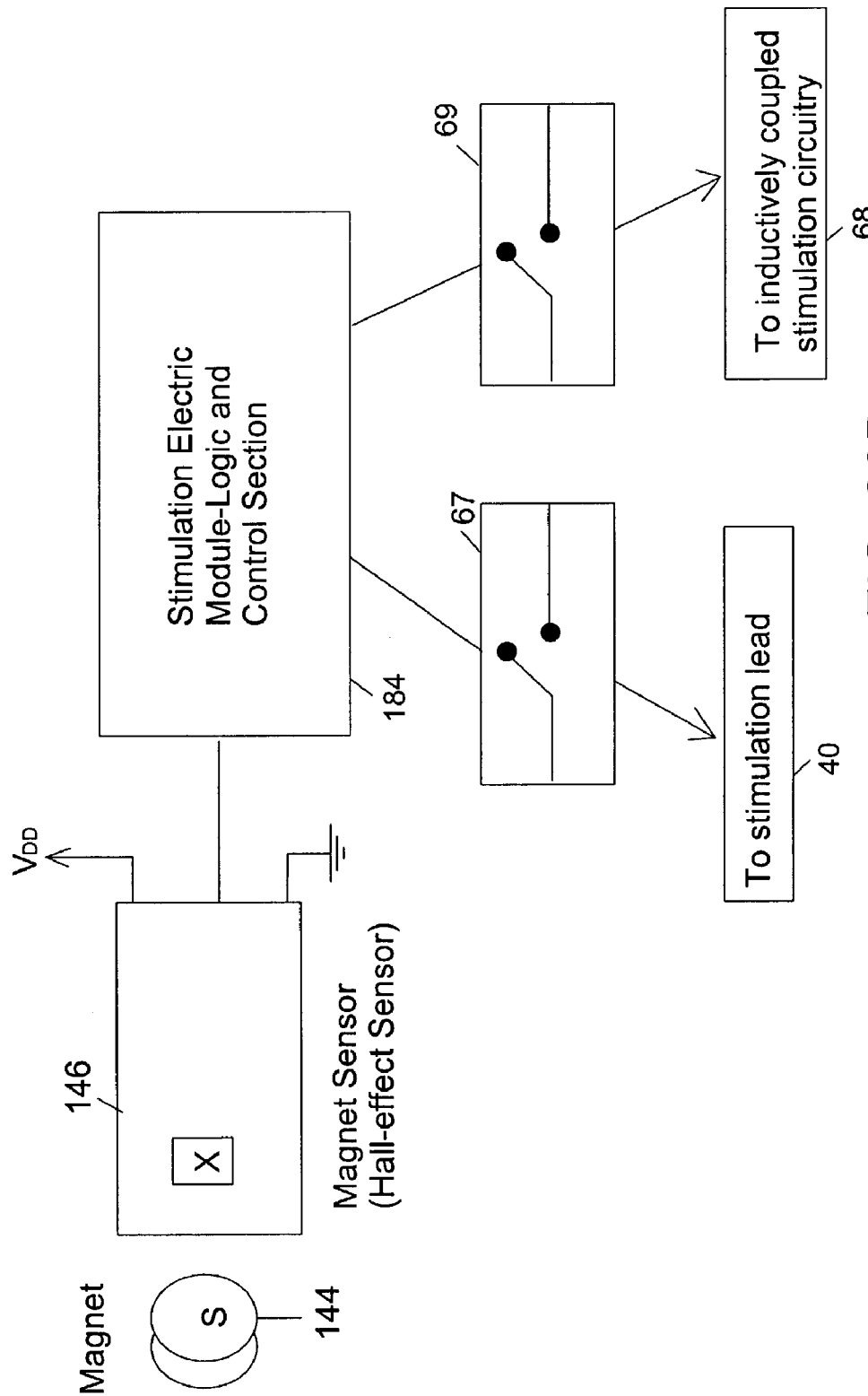
Figure 21:
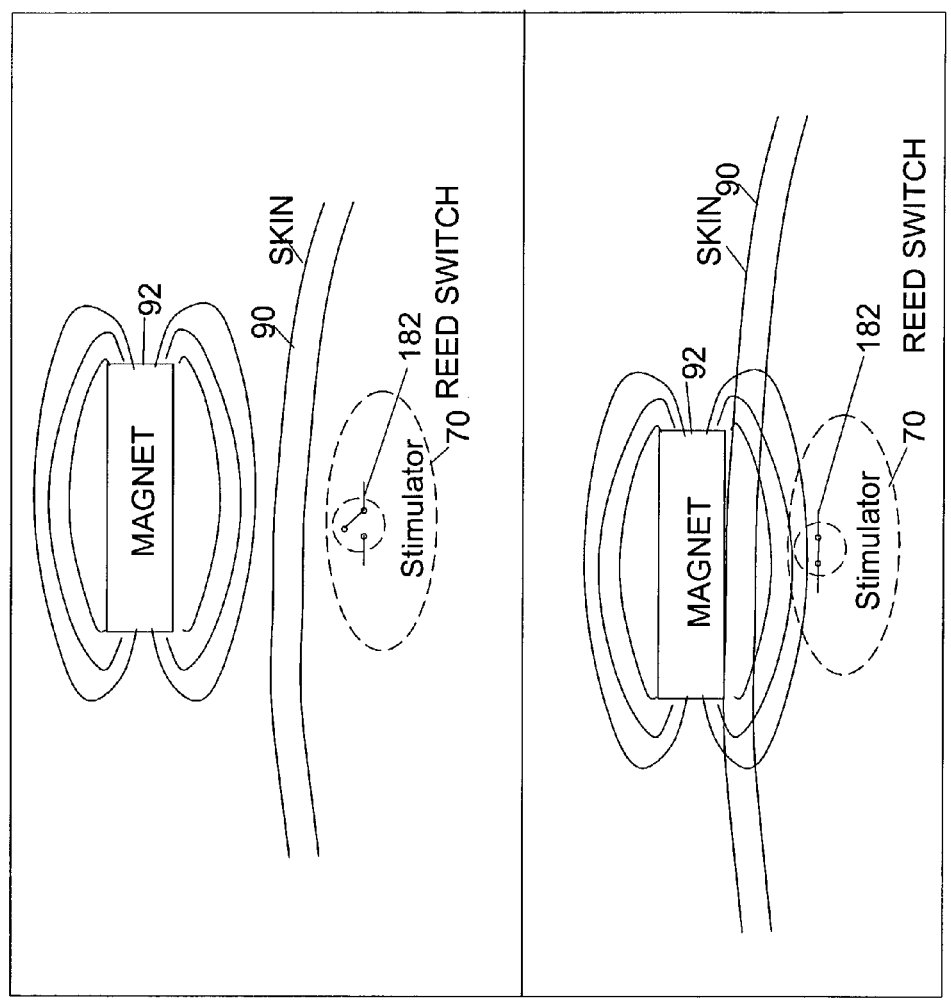
FIG. 21 is a diagram depicting the closure of a magnetic (Reed) switch with a magnet.

FIG. 20A is a simplified diagram of one aspect of control circuitry. In this embodiment, to program the implanted portion of the stimulator, a magnet is placed over the implanted pulse generator 70, causing a magnetically controlled Reed Switch 182 (which is normally in the open position) to be closed (shown in FIG. 21). As is also shown in FIG. 20A, at the same time a switch 67 going to the stimulator lead 40, and a switch 69 going to the circuit of the stimulus receiver module 68 are both opened, completely disconnecting both subassemblies electrically. Alternatively, as shown in FIG. 20B, instead of a reed switch 182, a solid state magnet sensor (Hall-effect sensor) 146 may be used for the same purpose. In the presently preferred embodiment, the solid state magnet sensor 146 is preferred, since there are no moving parts that can get stuck.

With the magnet sensor switch 146 (or Reed Switch 182) in the closed position, a coil 192 in the head of the programmer, communicates with a telemetry coil 172 (shown in FIG. 15) of the implanted pulse generator 70. Bidirectional inductive telemetry is used to exchange data with the implanted unit 70 by means of the external programming unit 85. Inductive coupling is also employed to transmit the programming instructions, which are detected by a receiving element, which is the antenna coil 172. These pulses of the magnetic field are transmitted in a coding scheme that induces current to flow in the antenna coil 172. Programming takes place via a coil 172, a receiving amplifier, a decoder, a controller, and the register in which the temporary and permanent programs are stored. Radiofrequency (RF) waves of the electromagnetic field using frequencies of approximately 100 KHz, that allow rapid transmission of large amounts of information. Both the transmitter (in the programmer) and the receiver (in the pulse generator 172) have antennae (coils) for emitting and decoding RF signals. The RF frequency is modulated, allowing the encoding of information during transmission by the programmer 85. The receiver coil 172 is tuned through properly selected inductor-capacitor values to have unique sensitivity to the carrier frequency of the transmitted signals.

Figure 23:
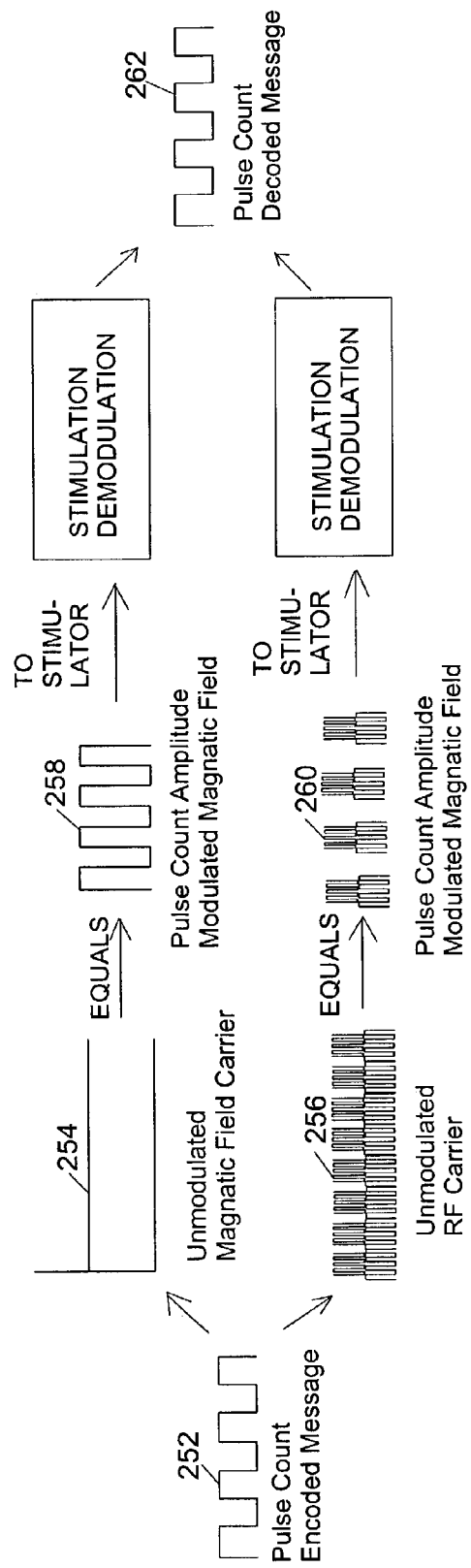
FIGS. 23A and 23B diagrammatically represent encoding and decoding of programming pulses.
Figure 23:
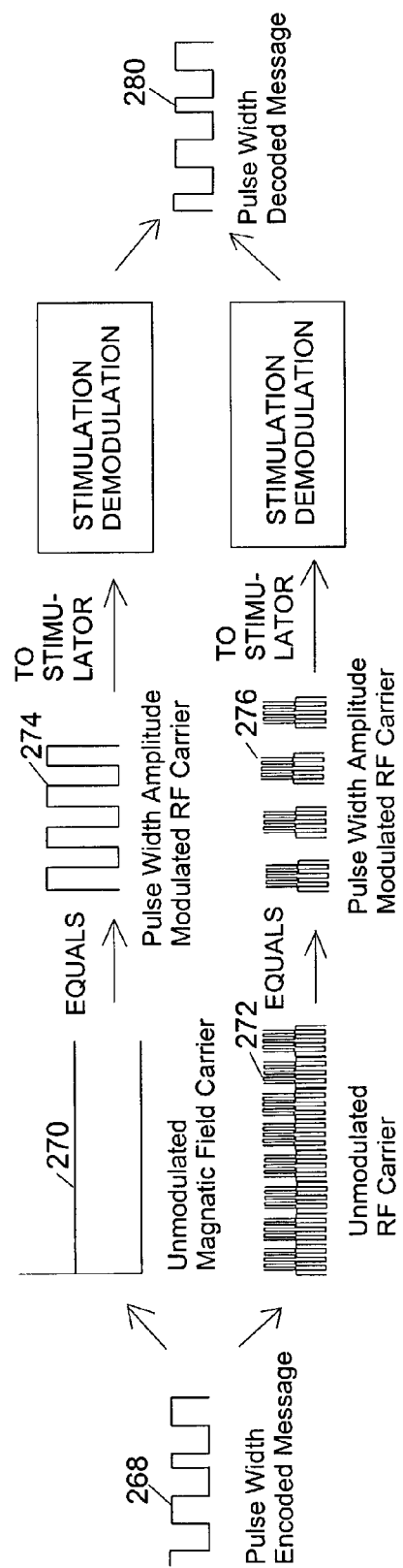

The transmission of programming information involves manipulation of the carrier signal in a manner that is recognizable by the pulse generator as a valid set of instructions (shown in conjunction with FIGS. 22A and 22B). The process of modulation serves as a means of encoding the programming instruction in a language that is interpretable by the pulse generator. Modulation of signal amplitude, pulse width, and time between pulses are all used in the programming system, as will be appreciated by those skilled in the art. FIG. 23A shows an example of pulse count modulation, and FIG. 23B shows an example of pulse width modulation.

Figure 24:
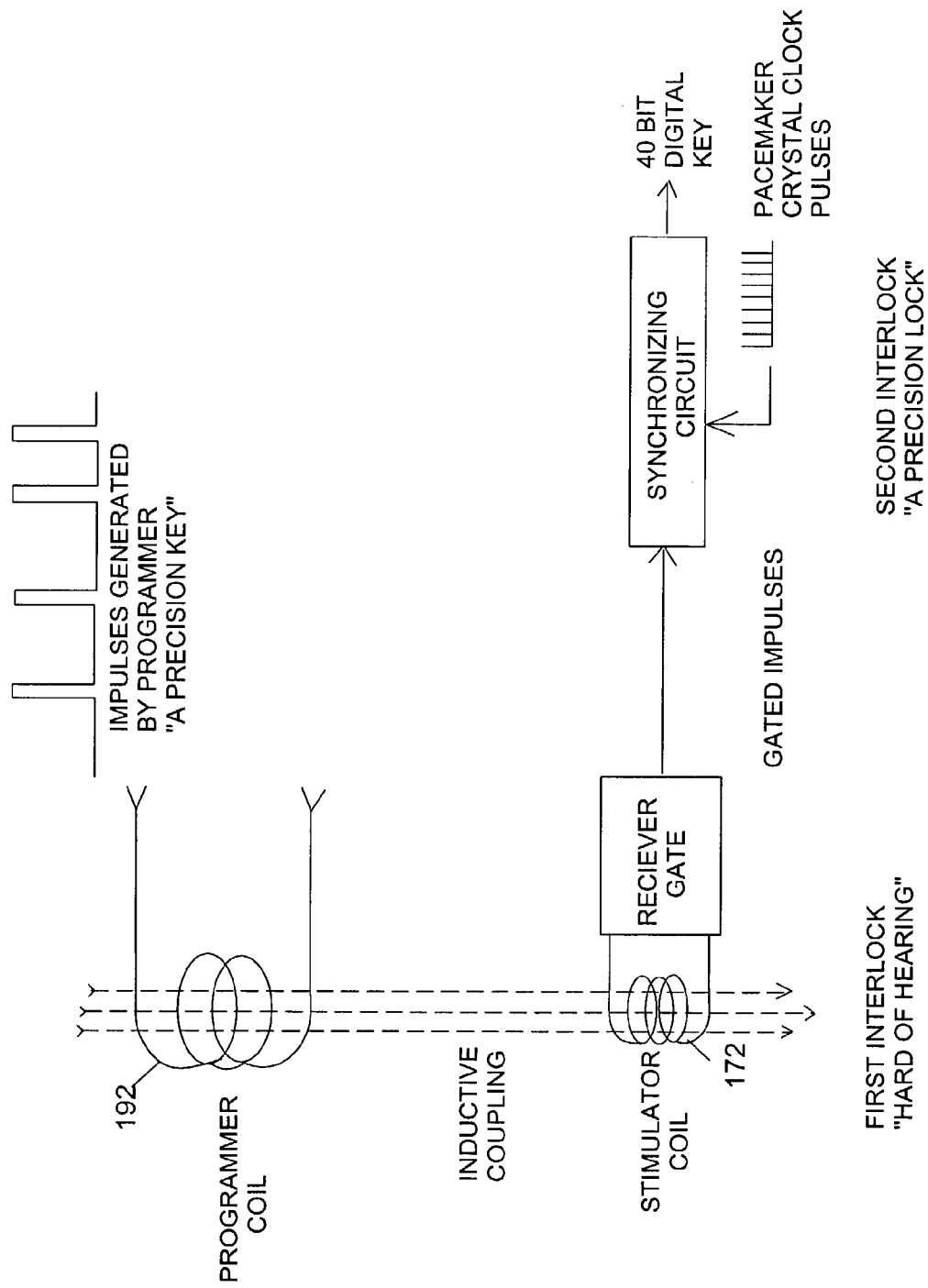
FIG. 24 diagrammatically represents secure communication for programming pulses.

The programming signal of the current system is designed to be secure. Several schemes can be used, as will be appreciated by those skilled in the art. For example, using the first group of bits and pulses as an identification or access code. Another example of programming signal security is shown in FIG. 24. An x number of pulses are organized into pairs to send a code message of x/2 digital bits that allow different levels of "safety interlocks".

Figure 25:
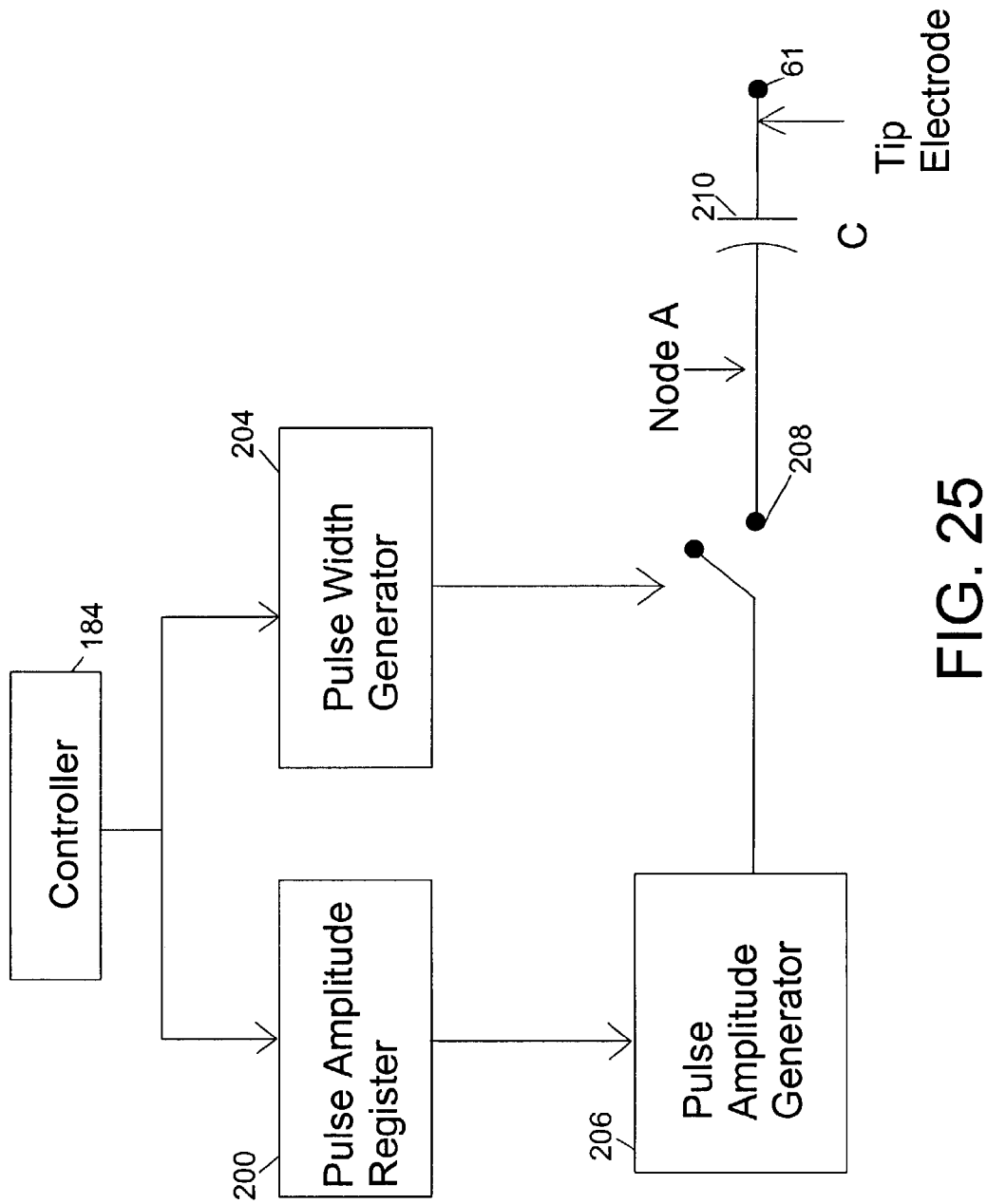
FIG. 25 is a block diagram for generation of a predetermined stimulation pulse.

Once the implanted pulse generator 70 is programmed, it operates continuously until a signal is received from the stimulus receiver module 68, via the high threshold comparator 178. As shown in FIG. 15, the controller 184 of the subassembly 70 controls the output amplifiers. The pulses have predetermined energy (pulse amplitude and pulse width) and are delivered at a time determined by the therapy stimulus controller. The circuitry in the output amplifier shown in conjunction with (FIG. 25), generates an analog voltage or current that represents the pulse amplitude. The stimulation controller module 184 initiates a stimulus pulse by closing a switch 208 that transmits the analog voltage or current pulse to the nerve tissue through the tip electrode 61 of the lead 40. The output circuit receiving instructions from the stimulus therapy controller 184 that regulates the timing of stimulus pulses and the amplitude and duration (pulse width) of the stimulus. The pulse amplitude generator 206 determines the configuration of charging and output capacitors necessary to generate the programmed stimulus amplitude. The output switch 208 is closed for a period of time that is controlled by the pulse width generator 204. When the output switch 208 is closed, a stimulus is delivered to the tip electrode 61 of the lead 40.

Figure 26:
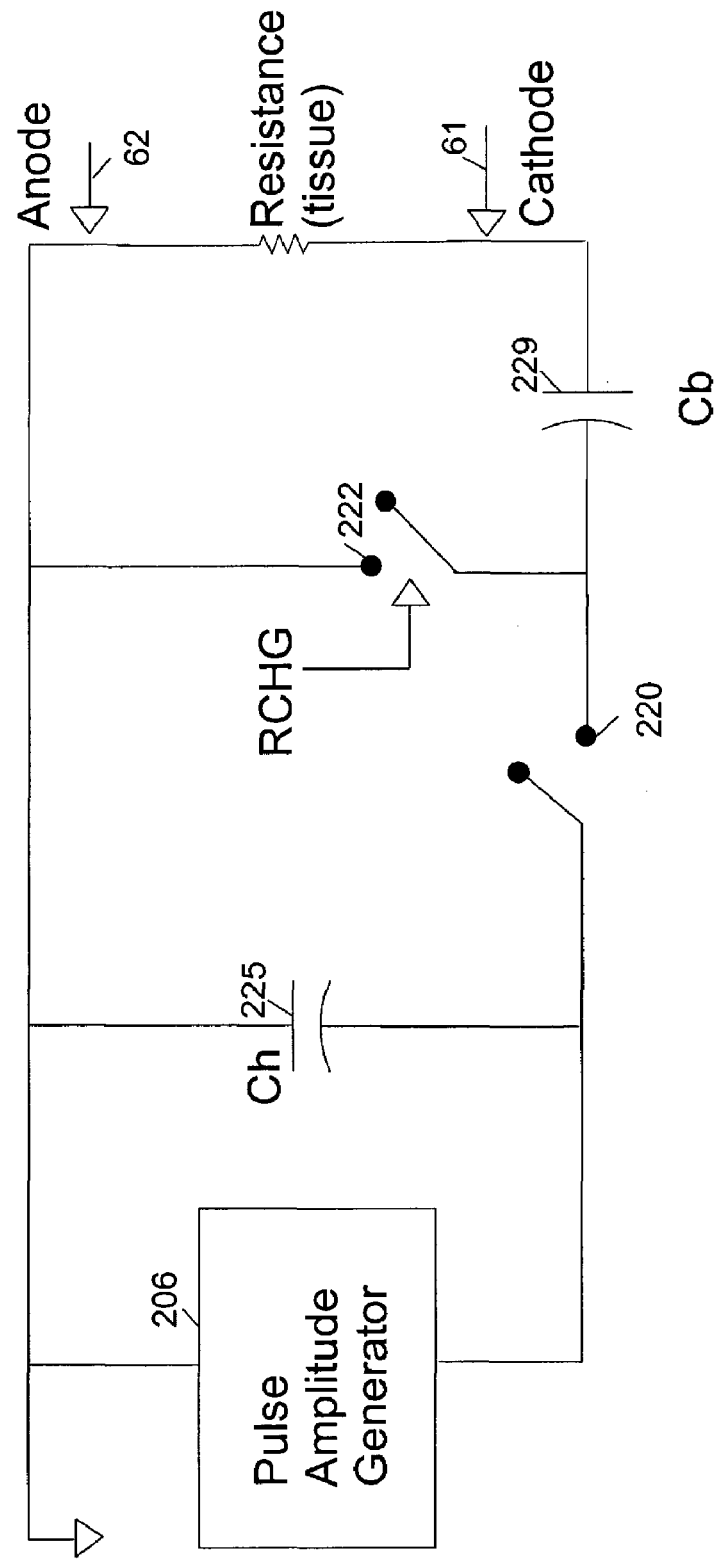
FIG. 26 is a schematic for delivering stimulation pulses.

The constant-voltage output amplifier applies a voltage pulse to the distal electrode (cathode) 61 of the lead 40. A typical circuit diagram of a voltage output circuit is shown in FIG. 26. This configuration contains a stimulus amplitude generator 206 for generating an analog voltage. The analog voltage represents the stimulus amplitude and is stored on a holding capacitor $C_h$ 225. Two switches are used to deliver the stimulus pulses to the lead 40, a stimulating delivery switch 220, and a recharge switch 222, that reestablishes the charge equilibrium after the stimulating pulse has been delivered to the nerve tissue. Since these switches have leakage currents that can cause direct current (DC) to flow into the lead system 40, a DC blocking capacitor $C_b$ 229, is included. This is to prevent any possible corrosion that may result from the leakage of current in the lead 40. When the stimulus delivery switch 220 is closed, the pulse amplitude analog voltage stored in the ($C_h$ 225) holding capacitor is transferred to the cathode electrode 61 of the lead 40 through the coupling capacitor, $C_b$ 229. At the end of the stimulus pulse, the stimulus delivery switch 220 opens. The pulse duration being the interval from the closing of the switch 220 to its reopening. During the stimulus delivery, some of the charge stored on $C_h$ 225 has been transferred to $C_b$ 229, and some has been delivered to the lead system 40 to stimulate the nerve tissue.

To re-establish equilibrium, the recharge switch 222 is closed, and a rapid recharge pulse is delivered. This is intended to remove any residual charge remaining on the coupling capacitor $C_b$ 229, and the stimulus electrodes on the lead (polarization). Thus, the stimulus is delivered as the result of closing and opening of the stimulus delivery 220 switch and the closing and opening of the RCHG switch 222. At this point, the charge on the holding $C_h$ 225 must be replenished by the stimulus amplitude generator 206 before another stimulus pulse can be delivered.

Referring back to FIG. 15, for the implanted power source, lithium iodine is preferred in the current embodiment, because of its long history in cardiac pacemakers. However, other power sources where lithium is combined with other cathode materials may be used, such as lithium cooper sulfide, lithium silver vanadium pentoxide, lithium bromine chloride, or lithium sulfuryl chloride cell.

FIG. 27A shows an example of the pulse trains that are delivered. The microcontroller is configured to deliver the pulse train as shown in FIG. 27B such that there is ramping up and ramping down, of the pulse train. The purpose of the ramping is to avoid sudden changes in stimulation, when the pulse train begins or ends.

Figure 28:
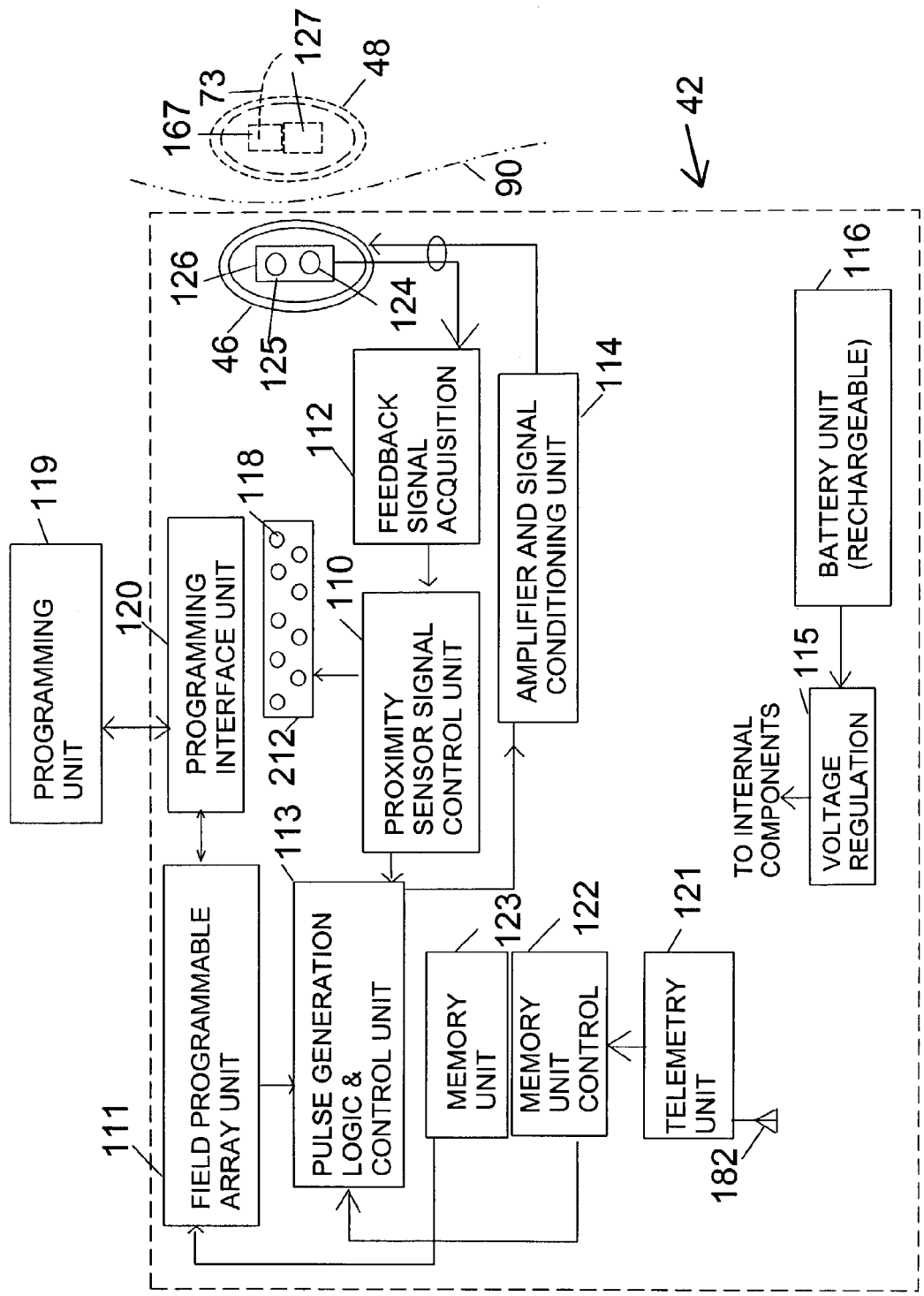
FIG. 28 is a functional block diagram of the external stimulator.

As shown in FIG. 28, the external pulse generator 42 is composed of three modules or sub-assemblies. The first sub-assembly is the pulse generation and signal conditioning components 113,114 the second is the battery 116, and the third is the telemetry and memory unit 121. The presently preferred embodiment, comprises proximity sensing and feedback circuitry, even though the pulse generator is able to function as supplier of electric pulses to the nerve tissue without the proximity feedback loop and the telemetry module. These modules or sub-assemblies also provide for a scalable external pulse generator 42. In the telemetry module, a wireless antenna 129 provides a means of communication to the external pulse generator 42 and the wireless remote server 189. A programming unit 119 can be physically connected to the stimulator 42 (via the Programming Unit Interface 120) in a tethered manner for loading of new predetermined programs or changing parameters of an existing program.

Also shown in conjunction with FIG. 28, the pre-packaged programs are stored in the memory unit 123. This represents memory with a readable and writeable portion and a non-volatile pre-programmable portion. A Field Programmable Array Unit (FPGA) 111 and a random access component (RAM) and Random addressable storage logic, facilitates the application of logic to edit and change the "current" parameters being utilized for pulse generation. The programmable unit interface 120 provides an interface to a programming unit (portable computer system) 119, which allows re-loading of a new set of predetermined programs. The pulse generation component 113 generates pulses of well-defined parameters, selected from the programmed parameters that exist in the memory unit 123. The pulse signal generation unit 113 provides its signal to be amplified and conditioned at the amplifier and signal conditioning unit 114 which then provides these signals to the primary (external) inductive coil 46. In one embodiment, the sensor unit 126 has a pair of sensors which senses the position of the implanted magnet 127, and the sensor signal is fed back to the proximity sensor control block 110 via the feedback signal conditioning unit 112. The feedback signal provides a proportional signal for modification of the frequency, amplitude and pulse-width of the pulse being generated by the pulse signal generator unit 113. The sensor unit 126 has two sensors 124, 125 that sense the location of the implanted magnet 127. The implanted (secondary) coil 48 is rigidly connected to the passive circuit and magnet 127. The skin 90 separates the subcutaneous and external components. The external components are placed on the skin, with the primary coil 46 in close proximity and optimally situated with respect to the implanted (secondary) coil 48.

Figure 29:
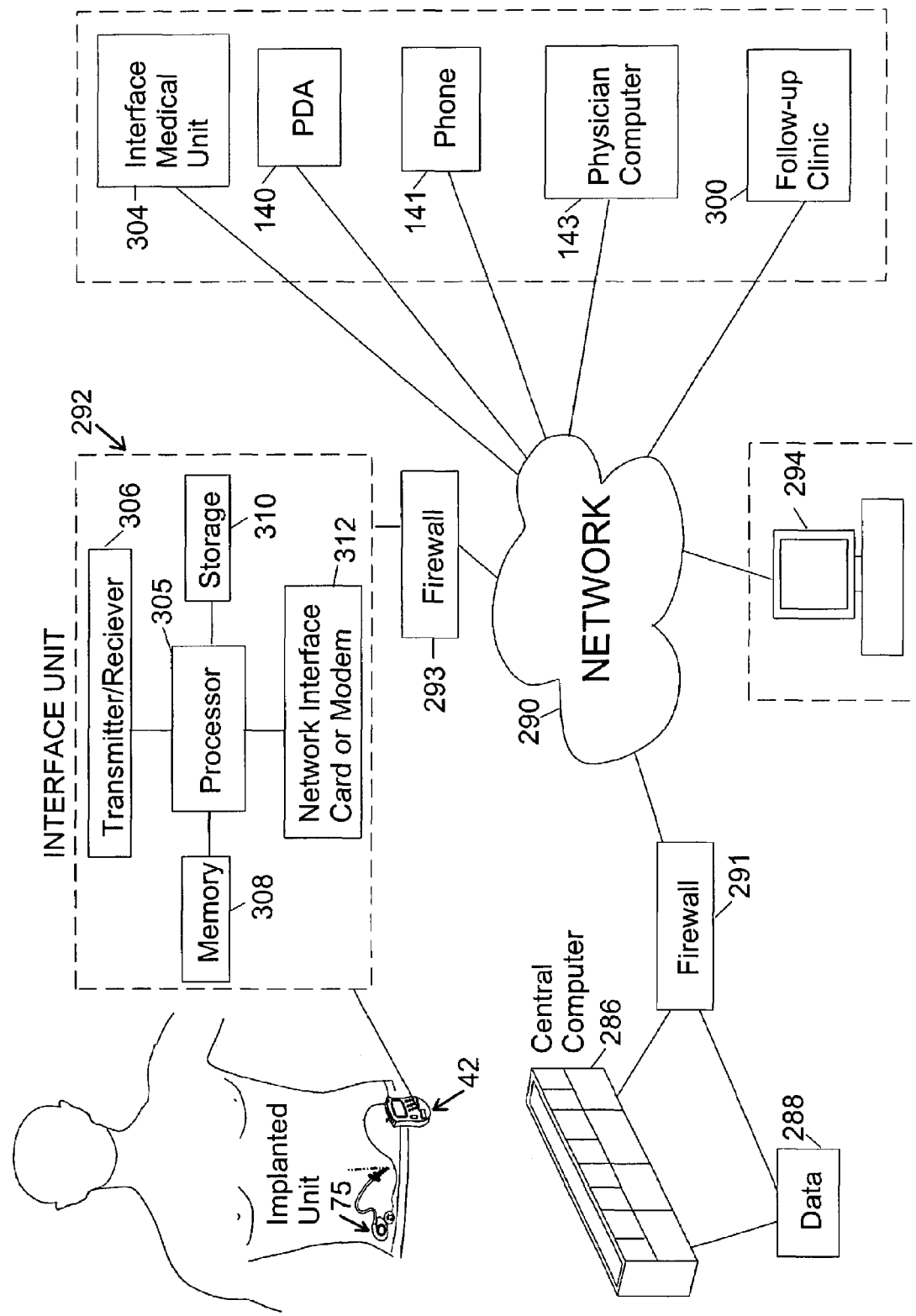
FIG. 29 is a block diagram of the networking interface board.

As shown in FIG. 29, in one aspect of the invention the external stimulator 42 and the programmer 85 are capable of being networked 290 to a central collaboration computer 286 as well as other devices such as a remote computer 294, PDA 140, phone 141, physician computer 143. This also minimizes situations in which the physical transport of a patient to a particular clinical setting is required. The implanted unit 75 communicates with the external stimulator 42 via inductive coupling between primary 46 and secondary coil 48.

The interface unit 292 in the preferred embodiment communicates with the central collaborative network 290 via land-lines such as cable modem or wirelessly via the internet. A central computer 286 which has sufficient computing power and storage capability to collect and process large amounts of data, contains information regarding device history and serial number, and is in communication with the network 290. Communication over collaboration network 290 may be effected by way of a TCP/IP connection, particularly one using the internet, as well as a PSTN, DSL, cable modem, LAN, WAN or a direct dial-up connection.

The standard components of interface unit shown in block 292 are processor 305, storage 310, memory 308, transmitter/receiver 306, and a communication device such as network interface card or modem 312. In the preferred embodiment these components are embedded in the external stimulator 42 and can alternatively be embedded in the programmer 85. These can be connected to the network 290 through appropriate security measures 293.

Another type of remote unit that may be accessed via central collaborative network 290 is remote computer 294. This remote computer 294 may be used by an appropriate attending physician to instruct or interact with interface unit 292, for example, instructing interface unit 292 to send instruction downloaded from central computer 286 to remote implanted unit 75.

Figure 30:
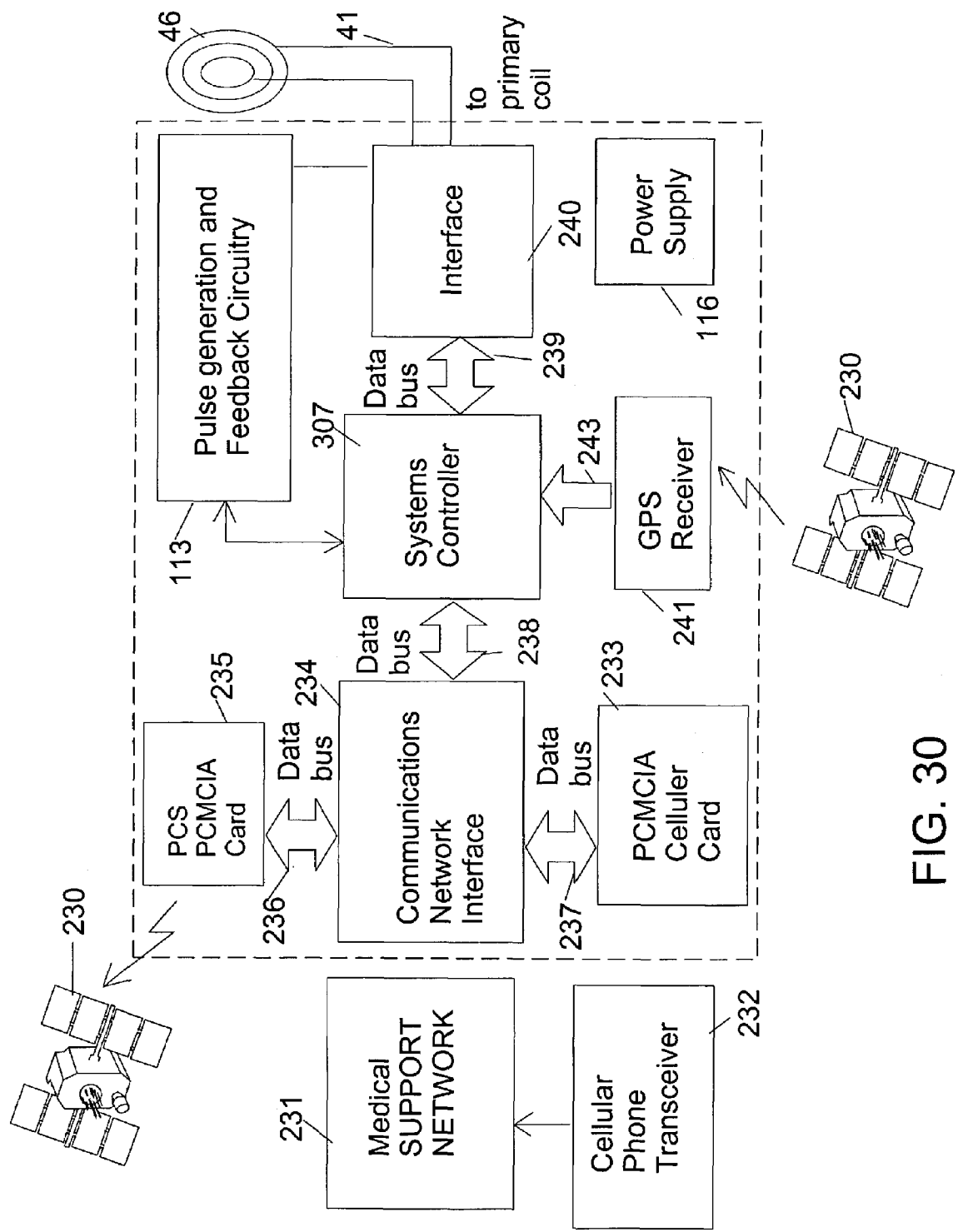
FIG. 30 is block diagram of the location tracking interface board.

In one embodiment of the system, as shown in conjunction with FIG. 30, the programmer 85 also comprises GPS receiver 241 for location tracking. Alternatively, the location tracking circuitry may be incorporated in the external stimulator 42. The system controller 307 contains a system lock for maintaining an accurate time base which may be re-calibrated periodically via accurate clocks in the GPS satellites 230. The microcomputer-based systems controller 307 is coupled to data communications network interface via data bus 238. The system controller 307 may be part of a standard or modified cellular telephone or other personnel communication device.

At a medical support network 231, a base station is provided to be in the communication link with the patient-worn communication device. The base station is preferably a microprocessor-based system that includes the software and hardware needed for communication with the patients to locate the patient.

In accordance with one aspect of the invention, the system controller 307 is coupled to a GPS receiver 241 via bus 243 for receiving patient positioning data from an earth satellite 230. The GPS receiver 241 may use current systems such as the PCMCIA GPS Sensor. The GPS receiver 241 may be actuated by a command received through the system controller 307 from the medical support network 231 in the case of an emergency response.

Either or both PCMCIA cards 235 and 233 may be provided and they are coupled with the voice and communications network 234 via buses 236 and 237. When both are provided access to the communications satellite link 230 is automatically obtained when a link to a cellular transceiver 232 is not possible.

Figure 31:
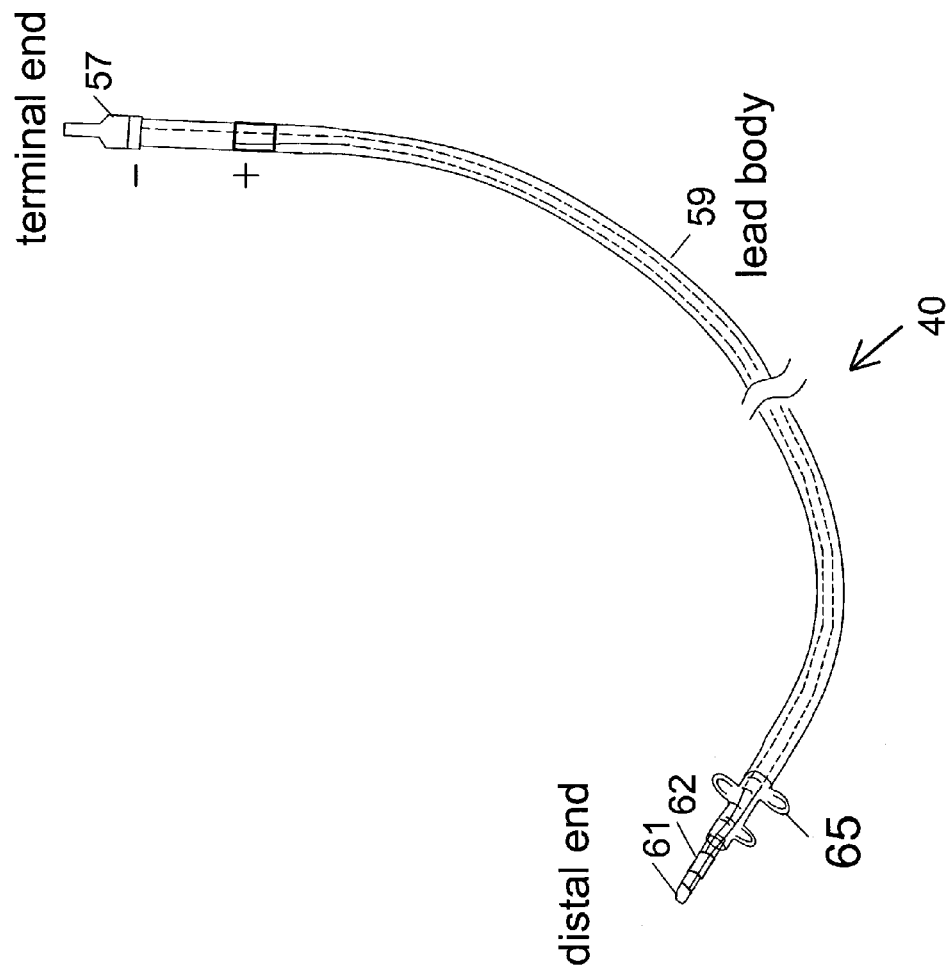
FIG. 31 is a diagram of an implantable lead.

Moving now to FIG. 31, the implanted lead 40 component of the system is similar to cardiac pacemaker leads, except for distal portion of the lead. In the presently preferred embodiment, the lead terminal is a linear bipolar (though a bifurcated terminal can also be used), and plug(s) into the cavity of the pulse generator 75. The lead body insulation 59 may be constructed of polyurethane, medical grade silicone, or silicone reinforced with polytetrafluoro-ethylene (PTFE). The electrodes for stimulating the sacral nerves may be elliptical shaped. These stimulating electrodes may be made of pure platinum, platinum/Iridium alloy or platinum/iridium coated with titanium nitride. The conductor connecting the terminal to the electrodes is made of an alloy of nickel-cobalt.

The choices for implanted lead design variables are also summarized in the table below.

Table of lead design variables

| Proximal End | | | | | Distal End |
|---|---|---|---|---|---|
| Lead Terminal | Lead body-Insulation Materials | Lead-Coating | Conductor (connecting proximal and distal ends | Electrode - Material | Electrode - Type |
| Linear Bipolar | Polyurethane | Antimicrobial coating | Alloy of Nickel-Cobalt | Pure Platinum | Elliptical electrode |
| Bifurcated | Silicone | Anti-Inflamatory coating | | Platinum-Iridium (Pt/IR) Alloy | Steroid eluting |
| | Silicone with Polytetrafluoro-ethylene (PTFE) | Lubricious coating | | Pt/Ir coated with Titanium Nitride | |
| | | | | Carbon | |

Once the lead 40 is fabricated, coating such as anti-microbial, anti-inflammatory, or lubricious coating may be applied to the body of the lead.

Figure 32:
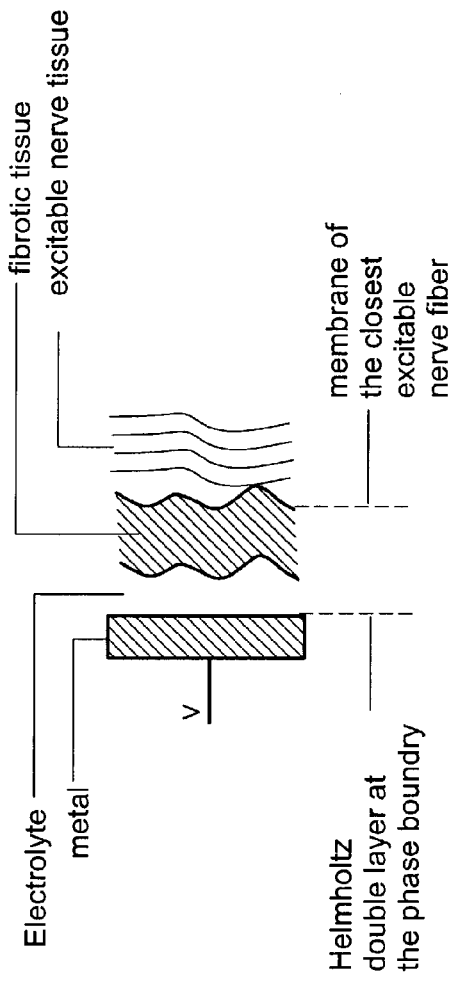
FIG. 32A is diagram depicting stimulating electrode-tissue interface.
FIG. 32B is diagram depicting electrical model of the electrode-tissue interface.
Figure 32:
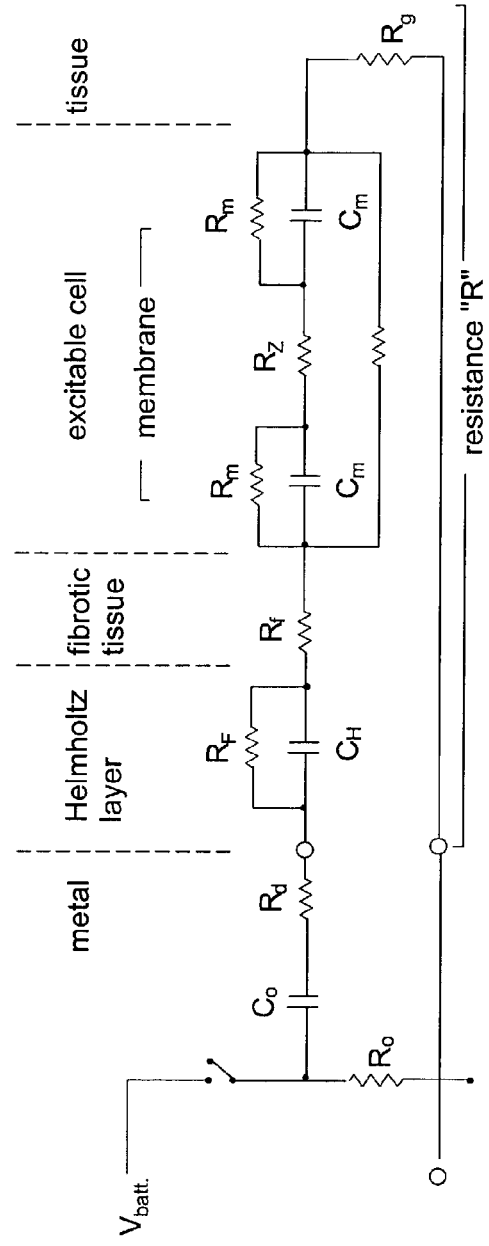

FIG. 32A summarizes an electrode-tissue interface. There is a thin layer of fibrotic tissue between the stimulating electrode 61 and the excitable nerve fibers of the sacral nerves 54. FIG. 32B summarizes the most important properties of the metal/tissue phase boundary in an equivalent circuit diagram. Both the membrane of the nerve fibers and the electrode surface are represented by parallel capacitance and resistance. Application of a constant battery voltage $V_{bat}$ from the pulse generator 75, produces voltage changes and current flow, the time course of which is crucially determined by the capacitive components in the equivalent circuit diagram. During the pulse, the capacitors $C_o$, $C_h$ and $C_m$ are charged through the ohmic resistances, and when the voltage $V_{bat}$ is turned off, the capacitors discharge with current flow on the opposite direction.

Figure 33:
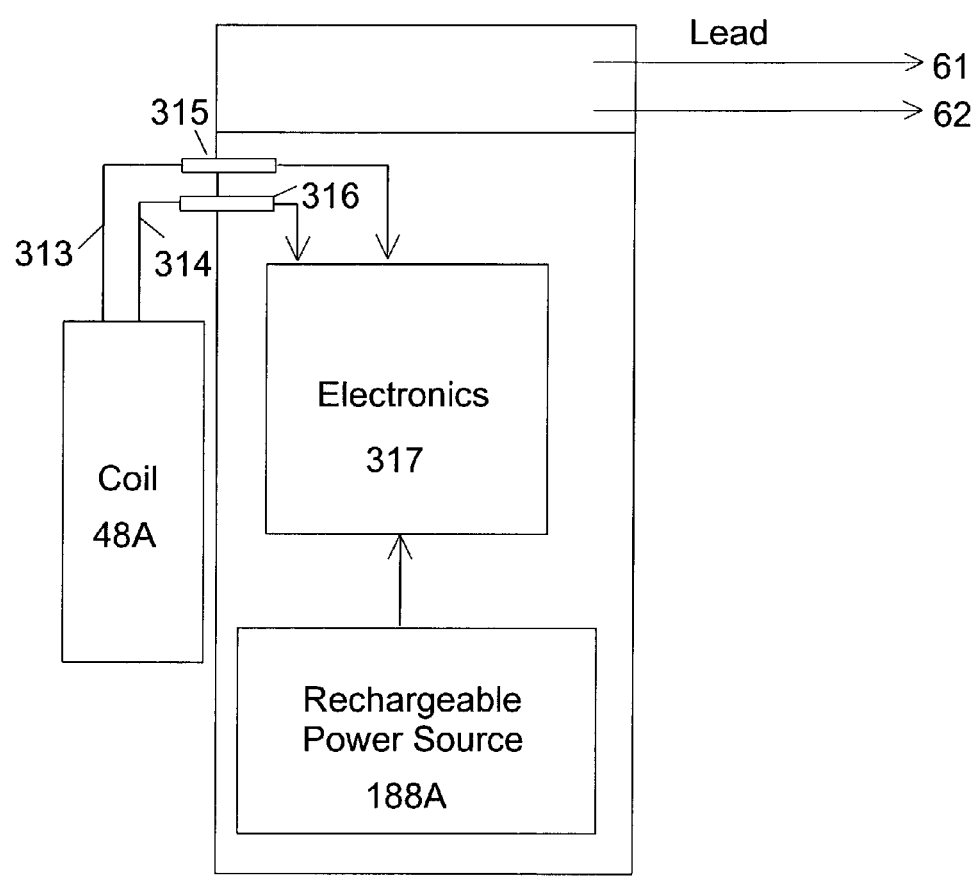
FIG. 33 depicts an embodiment where the system is used as an implantable, rechargeable system.

One of ordinary skill in the art will appreciate that with some modification in the circuitry the same concept can be adapted for an implantable, rechargeable power source. In such an embodiment (shown in conjuction with FIG. 33), the RF pulses transmitted via coil 46 and received via subcutaneous coil 48A are rectified via diode bridge 154. These DC pulses are processed and the resulting current applied to recharge the battery 188A in the implanted pulse generator.

Figure 34:
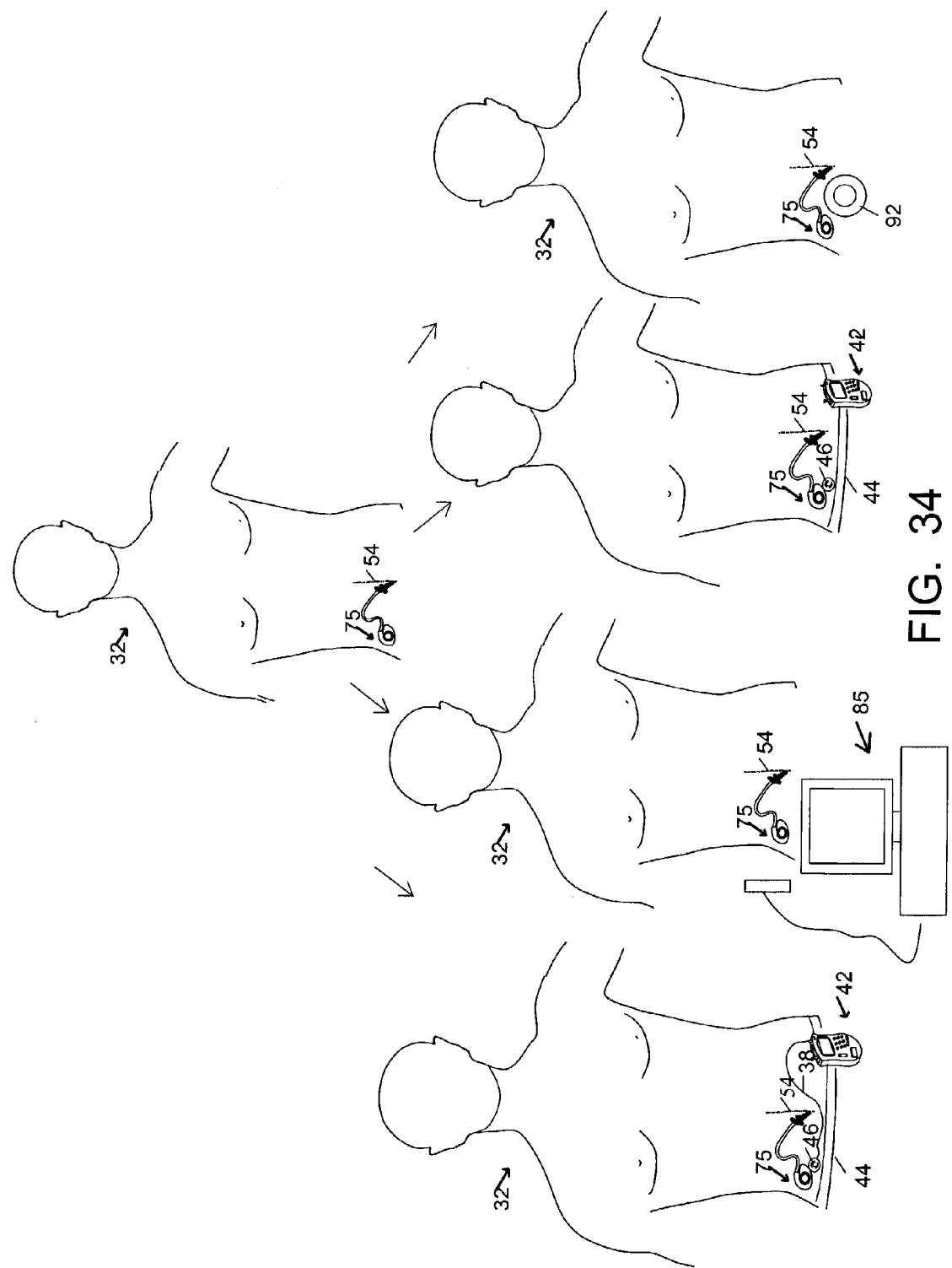
FIG. 34 is a diagram depicting different varieties of the system of the invention.

It will also be obvious to one of ordinary skill in the art that, the current invention can be practiced with a cheaper and less programmable version of an implantable pulse generator. For example, as shown in FIG. 34 (bottom right), a programmer-less stimulator may be used, where a limited number of programs may be accessed via a magnet, preferably as disclosed in U.S. Pat. No. 6,449,512 and incorporated here by reference.

Figure 35:
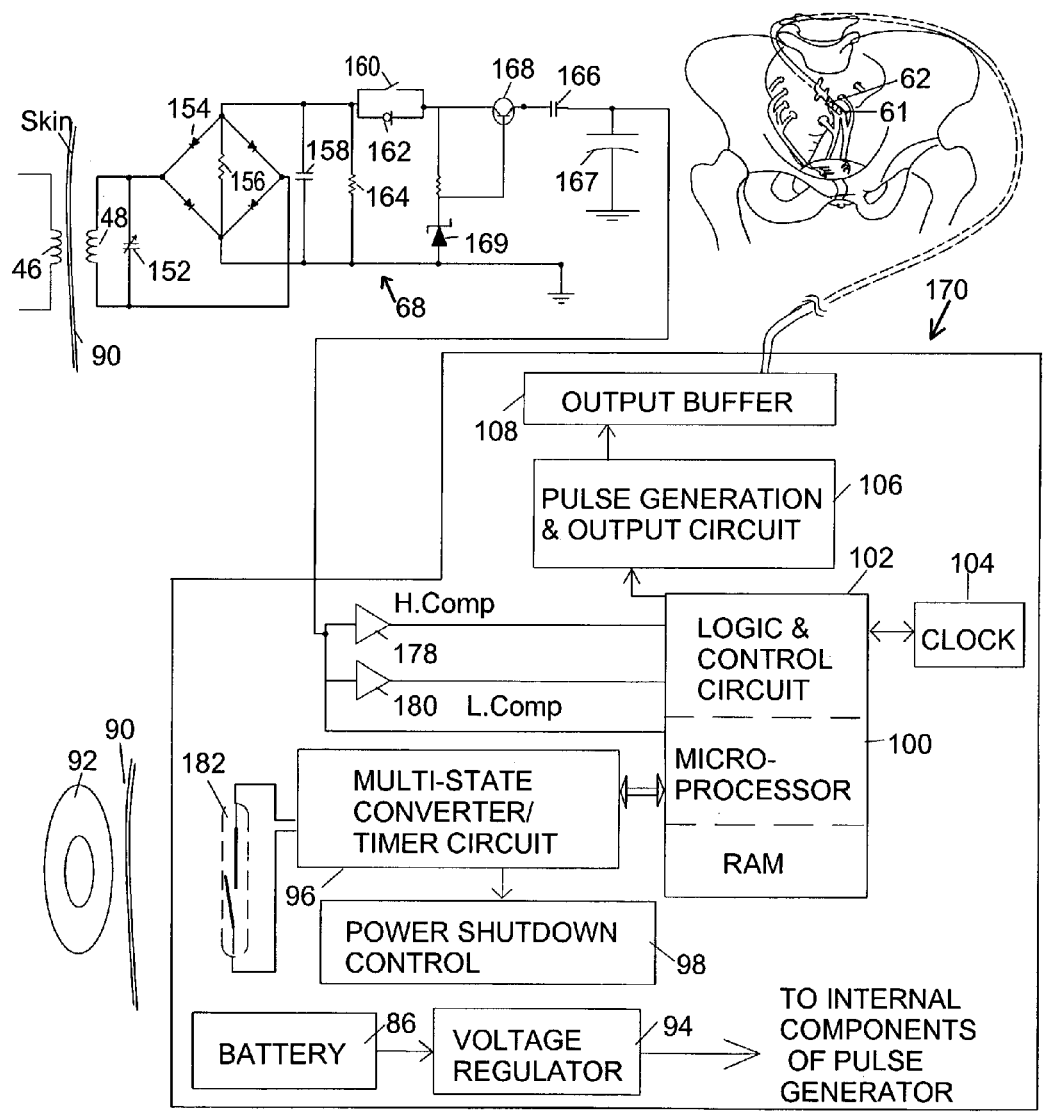
FIG. 35 is a schematic and block diagram depicting a simpler version of the pulse generator.

As shown with reference to FIG. 35, in this version only a limited number of states are possible. For example LO, MED, MED-HI, HI stimulation states and an OFF state. Each state corresponds to a complete program comprising a unique combination of pulse amplitude, pulse width, pulses per second, ON-time and OFF-time. By using just a magnet 92, each of these states can be programmed by swiping the magnet 92, different number of times. For example, once, twice, three times etc. Once the pulse generator 170 is programmed to a particular state, it supplies stimulation pulses to the sacral nerves 54 according to the programmed state, until stimulation energy is received from the inductively coupled part of the system 68. When energy is received from inductively coupled part of the system 68, the battery operated portion goes into "sleep mode" for a predetermined period of time which is programmed.

Figure 36:
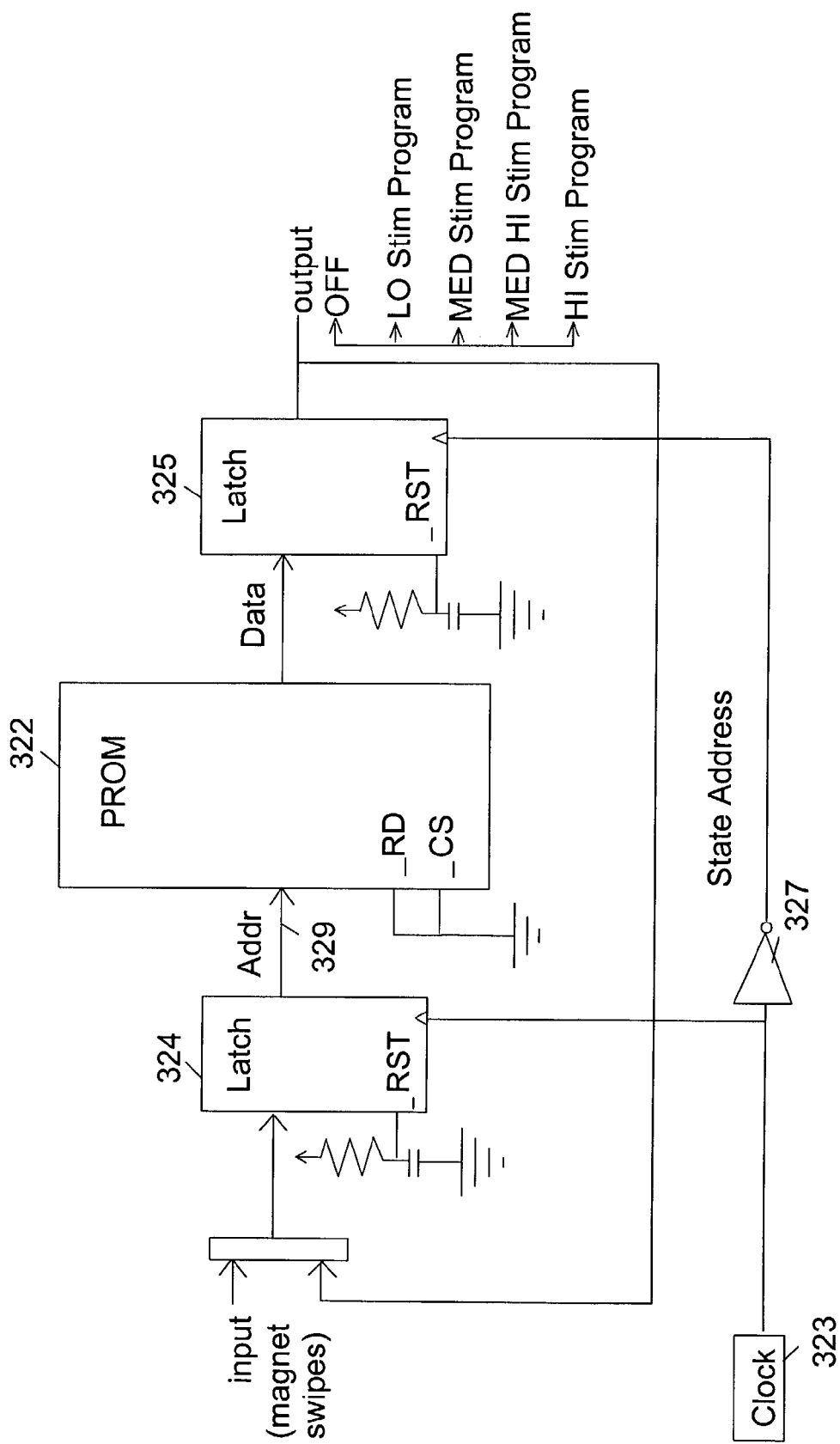
FIG. 36 is a schematic diagram depicting digital circuitry for state machine.

FIG. 36 shows a representative digital circuitry used for the basic state machine circuit. The circuit consists of a PROM 322 that has part of its data fed back as a state address. Other address lines 329 are used as circuit inputs, and the state machine changes its state address on the basis of these inputs. The clock 323 is used to pass the new address to the PROM 322 and then pass the output from the PROM 322 to the outputs and input state circuits. The two latches 324, 325 are operated 180° out of phase to prevent glitches from unexpectedly affecting any output circuits when the ROM changes state. Each state responds differently according to the inputs it receives.

Thus, in this embodiment the functioning of the system is similar to as described earlier. This embodiment though is cheaper to produce and offers limited programmability of the battery operated part of the system.

While the invention herein disclosed has been described by means of specific embodiments and applications thereof, numerous modifications and variation could be made thereto by those skilled in the art without departing from the scope of the invention set forth in the claims.

What is claimed is:

1. A method to provide electrical pulses to a sacral plexus of a patient to provide therapy for at least one of urinary incontinence and urological disorders, comprising the steps of:
providing an implanted stimulator, wherein said implanted stimulator comprises a microprocessor based programmable pulse generator module and a stimulus receiver module that receives external stimulus signals and is capable of applying said electrical pulses independently of said pulse generator module;
providing an external programmer for programming said electrical pulses of said implanted stimulator;
providing an external stimulator for inductively coupling to said stimulus receiver module;
providing control circuitry that selectively operates one of said implanted pulse generator module and said stimulus receiver module; and
providing an implanted lead in electrical contact with said implanted stimulator, and at least one electrode adapted to be in contact with said sacral plexus;
whereby said electrical pulses are provided to said sacral plexus of a patient.

2. Method of claim 1, wherein said urinary incontinence and urological disorders further comprises treatment for at least one of urge incontinence, overflow incontinence, stress incontinence, functional incontinence, neuro-urological disorders, bladder control, bladder inflammation, and bladder pain such as may be caused by interstitial cystitis disease or the like.

3. Method of claim 1, wherein said stimulus receiver further comprises a coil and circuitry.

4. Method of claim 1, wherein said external stimulator further comprises telemetry circuitry.

5. Method of claim 1, wherein said external stimulator comprises means for networking with remote computers.

6. Method of claim 1, wherein said external programmer comprises a global positioning system (GPS) module for determining patient location.

7. Method of claim 1, wherein said Implanted pulse generator module further comprises rechargeable power source, and is adapted to be recharged using an external power source.

8. Method of claim 1, wherein said electric pulses provided by said external stimulator and said stimulus receiver overrides said electric pulses provided by said implanted pulse generation module.

9. A method to stimulate a sacral plexus of a patient using pulsed electrical stimulation to provide therapy for at least one of urinary incontinence and urological disorders, comprising the steps of:
providing an implanted stimulator, wherein said implanted stimulator comprises a microprocessor based programmable pulse generator module and a stimulus receiver module that receives external stimulus signals and is capable of applying said electrical pulses independently of said pulse generator module;
providing an external stimulator with adjustable programs of stimulation for inductively coupling to said implanted stimulus receiver;
providing an external programmer for programming said implanted stimulator;
providing a lead connected with said implanted stimulator, and at least one electrode adapted to be in contact with said sacral plexus;
determining suitable stimulation program for said patient, using said external stimulator; and
programming said implanted stimulator with said suitable stimulation program using said external program,
whereby said pulsed electrical stimulation is delivered to said sacral plexus.

10. Method of claim 9, wherein said urinary incontinence and urological disorders further comprises treatment for at least one of urge incontinence, overflow incontinence, stress incontinence, functional incontinence, neuro-urological disorders, bladder control, bladder inflammation, and bladder pain such as may be caused by interstitial cystitis disease or the like.

11. A method of claim 9, wherein said implanted stimulator further comprises control circuitry that selectively operates one of said implanted pulse generator module and said stimulus receiver module.

12. Method of claim 9, wherein said external stimulator further comprises telemetry circuitry.

13. Method of claim 9, wherein said external stimulator comprises means for networking with remote computers.

14. Method of claim 9, wherein said external programmer means further comprises a global positioning system (GPS) receiver means for patient location.

15. A system to neuromodulate sacral plexus of a patient, comprising:

an implantable stimulator, wherein said implantable stimulator comprising a microprocessor based programmable pulse generator module and a stimulus receiver module that receives external stimulus signals and is capable of applying said electrical pulses independently of said pulse generator module;

an external stimulator to provide stimulation pulses by inductively coupling to said stimulus receiver;

an external programmer for programming said implantable stimulator;

control circuitry to selectively operate one of said implantable pulse generator module and said stimulus receiver module; and an implantable lead with at least one electrode adapted to be in contact with said sacral plexus.

16. System of claim 15, wherein said external stimulator further comprises telemetry circuitry.

17. System of claim 15, wherein said external stimulator comprises means for networking with remote computers.

18. System of claim 15, wherein said external stimulator comprises a global positioning system (GPS) module for determining patient location.

19. System of claim 15, wherein said implanted pulse generator module further comprises rechargeable power source.

20. System of claim 15, wherein said external stimulator can be utilized to titrate said neuromodulation provided to said sacral plexus.

21. A system for providing pulsed electrical stimulation to sacral nerves of a patient to provide therapy for at least one of urinary incontinence and urological disorders, comprising:

an implantable stimulator, wherein said implantable stimulator comprising a pulse generator module and a stimulus receiver module that receives external stimulus signals and is capable of applying said electrical pulses independently of said pulse generator module, wherein said implantable stimulator is programmable with a magnet;

an external stimulator to provide stimulation pulses by inductively coupling to said stimulus receiver;

control circuitry that selectively operates one of said pulse generator module and said stimulus receiver module; and an implantable lead with at least one electrode adapted to be in contact with said sacral nerves.

22. System of claim 21, wherein said urinary incontinence and urological disorders further comprises treatment for at least one of urge incontinence, overflow incontinence, stress incontinence, functional incontinence, neuro-urological disorders, bladder control, bladder inflammation, and bladder pain such as may be caused by interstitial cystitis disease or the like.

23. System of claim 21, wherein said external stimulator further comprises telemetry circuitry.

24. System of claim 23, wherein said telemetry circuit communicates over the internet.

25. System of claim 21, wherein said external stimulator is networked with remote computers.

26. System of claim 21, wherein said external stimulator comprises a global positioning system (GPS) module for determining patient location.

27. System of claim 21, wherein said implanted pulse generator further comprises rechargeable power source.

28. A system to provide therapy for at least one of urge incontinence, overflow incontinence, stress incontinence, functional incontinence, neuro-urological disorders, bladder inflammation, and bladder pain such as may be caused by interstitial cystitis disease or the like, comprising:

a programmable implantable stimulator, wherein said implantable stimulator comprises a microprocessor based programmable pulse generator module and a stimulus receiver module that receives external stimulus signals and is capable of applying said electrical pulses independently of said pulse generator module, wherein said implantable stimulator is adopted to be rechargeable with an external power supply;

control circuitry that selectively operates one of said pulse generator module and said stimulus receiver module;

an external power source to recharge said implanted stimulator;

an external programmer to program the electrical pulses of said implanted stimulator; and an implantable lead connectable to said implantable stimulator with at least one electrode adapted to be in contact with a sacral plexus or branches or parts thereof.

29. Method of claim 1, wherein said sacral plexus comprises sacral nerve roots S2, S3, S4 or peripheral branches or parts thereof.

* * * * *